(12) United States Patent
Senn-Bilfinger et al.

(10) Patent No.: US 7,189,736 B2
(45) Date of Patent: Mar. 13, 2007

(54) PRODRUGS OF IMIDAZOPYRIDINE DERIVATIVES

(75) Inventors: Jörg Senn-Bilfinger, Constance (DE); Wilm Buhr, Constance (DE)

(73) Assignee: Altana Pharma AG, Constance (DE)

( * ) Notice: Subject to any disclaimer, the term of this patent is extended or adjusted under 35 U.S.C. 154(b) by 171 days.

(21) Appl. No.: 10/826,337

(22) Filed: Apr. 19, 2004

(65) Prior Publication Data

US 2004/0198764 A1     Oct. 7, 2004

Related U.S. Application Data

(63) Continuation of application No. 10/182,619, filed as application No. PCT/EP01/03514 on Mar. 28, 2001, now abandoned.

(30) Foreign Application Priority Data

Mar. 29, 2000  (EP)  .................... 00106695

(51) Int. Cl.
| | |
|---|---|
| *A01N 43/42* | (2006.01) |
| *A61K 31/44* | (2006.01) |
| *C07D 471/00* | (2006.01) |
| *C07D 491/00* | (2006.01) |
| *C07D 498/00* | (2006.01) |

(52) U.S. Cl. .................... 514/293; 546/82; 546/83
(58) Field of Classification Search ................ 514/293; 546/82, 83
See application file for complete search history.

(56) References Cited

U.S. PATENT DOCUMENTS

| | | | |
|---|---|---|---|
| 4,468,400 A | 8/1984 | Gold et al. | |
| 4,673,679 A | 6/1987 | Aungst et al. ............... | 514/282 |
| 5,432,183 A | 7/1995 | Schulte ........................ | 514/291 |
| 6,160,119 A | 12/2000 | Senn-Bilfinger ............. | 543/83 |
| 6,197,783 B1 | 3/2001 | Senn-Bilfinger et al. .... | 514/293 |
| 6,384,048 B1 * | 5/2002 | Senn-Bilfinger ............. | 514/293 |
| 6,436,953 B1 | 8/2002 | Senn-Bilfinger ............. | 514/293 |
| 6,916,825 B2 * | 7/2005 | Senn-Bilfinger et al. .... | 514/293 |

FOREIGN PATENT DOCUMENTS

| | | |
|---|---|---|
| DE | 43 08 095 | 9/1994 |
| DE | 4308095 | * 9/1994 |
| WO | WO 98/27714 | 10/1995 |
| WO | 98/42707 | * 10/1998 |
| WO | WO 98/42707 | 10/1998 |
| WO | 98/54188 | * 12/1998 |
| WO | 00/26217 | * 10/1999 |
| WO | WO 98/54188 | 12/1999 |
| WO | WO 01/072754 | 10/2001 |

OTHER PUBLICATIONS

International Journa of Pharmaceutics, "Comparative study and optimisation of the administration mode of three proton pump inhibitors by nasogastric tube", vol. 299, pp. 65-72.*
Journal of Clinical Microbiology, "Detection of Helicobacter pulori in Gastric Mucosa of Patients with Gastroduodenal Diseases by PCR-Restriction Analysis Using the RNA Polymerase Gene (rpoB)", vol. 41, pp. 3387-3391.*
Bundgaard, H., *Design of Prodrugs*, Elsevier Science, pp. 1-3, (1985).

* cited by examiner

*Primary Examiner*—Margaret D. Seaman
*Assistant Examiner*—Niloofar Rahmani
(74) *Attorney, Agent, or Firm*—Nath & Associates PLLC; Gary M. Nath; Susanne M. Hopkins

(57) ABSTRACT

Compounds of formula 1, in which the substituents have the meanings mentioned in the description are suitable for the prevention and treatment of gastrointestinal diseases.

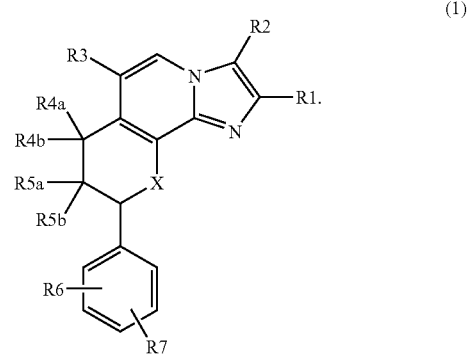

(1)

16 Claims, No Drawings

PRODRUGS OF IMIDAZOPYRIDINE DERIVATIVES

This application is a continuation of U.S. Ser. No. 10/182,619, filed Oct. 1, 2002 now abandoned, incorporated by reference herein in its entirety, which is a 371 of PCT/EP01/03514, filed on Mar. 28, 2001, which claims the priority of EP 00106695.0, filed on Mar. 29, 2000.

FIELD OF APPLICATION OF THE INVENTION

The invention relates to novel compounds which are used in the pharmaceutical industry as active compounds for the production of medicaments.

KNOWN TECHNICAL BACKGROUND

U.S. Pat. No. 4,468,400 describes tricyclic imidazo[1,2-a]pyridines with various ring systems fused to the imidazopyridine parent structure, which should be suitable for the treatment of peptic ulcers. —International Patent Application WO 95/27714 discloses certain substituted tricyclic imidazo[1,2-a]pyridines which are said to reversibly inhibit gastric acid secretion and to be useful in the prevention and treatment of gastrointestinal inflammatory diseases. International Patent Application WO 98/42707 discloses tetrahydroimidazo[1,2-h][1,7]naphthyridines which shall be suitable for the prevention and treatment of gastrointestinal diseases. WO 98/54188 describes fused dihydropyrans, which are said to be suitable for the treatment of peptic ulcer disorders. —In German Offenlegungsschrift 43 08 095, certain prodrug derivatives of pharmaceutically active agents with hydroxyl groups are disclosed.

DESCRIPTION OF THE INVENTION

The invention relates to compounds of the formula 1

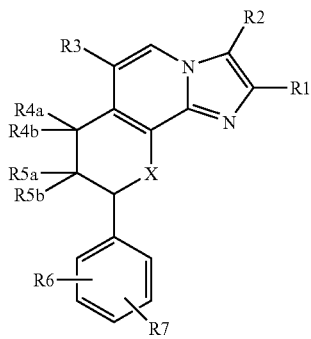

(1)

in which
R1 is hydrogen, 1–4C-alkyl or hydroxy-1–4C-alkyl,
R2 is hydrogen, 1–4C-alkyl, hydroxy-1–4C-alkyl, halogen, 2–4C-alkenyl or 2–4C-alkynyl,
R3 is hydrogen, halogen, trifluoromethyl, 1–4C-alkyl, 2–4C-alkenyl, 2–4C-alkynyl, carboxyl, —CO-1–4C-alkoxy, hydroxy-1–4C-alkyl, 1–4C-alkoxy-1–4C-alkyl, fluoro-1–4C-alkoxy-1–4C-alkyl or the radical —CO—NR3aR3b,
one of the substituents R4a and R4b is hydrogen and the other is hydroxyl, 1–4C-alkoxy, 1–4C-alkoxy-1–4C-alkoxy, 1–4C-alkylcarbonyloxy or the radical R4', or in which R4a and R4b together are O (oxygen),
where R4' is a radical from which a hydroxyl group is formed under physiological conditions,
one of the substituents R5a and R5b is hydrogen and the other is hydrogen, hydroxyl, 1–4C-alkoxy, 1–4C-alkoxy-1–4C-alkoxy, 1–4C-alkylcarbonyloxy or the radical R5', or in which R5a and R5b together are O (oxygen),
where R5' is a radical from which a hydroxyl group is formed under physiological conditions,
where one of the substituents R4a and R4b must have the meaning R4' and/or one of the substituents R5a and R5b must have the meaning R5',
R6 is hydrogen, halogen, 1–4C-alkyl, 1–4C-alkoxy, 1–4C-alkoxycarbonylamino, 1–4C-alkoxy-1–4C-alkoxycarbonylamino or trifluoromethyl,
R7 is hydrogen, halogen, 1–4C-alkyl or 1–4C-alkoxy and
X is O (oxygen) or NH,
where
R3a is hydrogen, 1–7C-alkyl, hydroxy-1–4C-alkyl or 1–4C-alkoxy-1–4C-alkyl and
R3b is hydrogen, 1–7C-alkyl, hydroxy-1–4C-alkyl or 1–4C-alkoxy-1–4C-alkyl,
or where
R3a and R3b together, including the nitrogen atom to which both are bonded, are a pyrrolidino, piperidino or morpholino radical, and their salts.

1–4C-Alkyl represents straight-chain or branched alkyl radicals having 1 to 4 carbon atoms. Examples which may be mentioned are the butyl radical, isobutyl radical, sec-butyl radical, tert-butyl radical, propyl radical, isopropyl radical, ethyl radical and the methyl radical.

Hydroxy-1–4C-alkyl represents abovementioned 1–4C-alkyl radicals which are substituted by a hydroxyl group. Examples which may be mentioned are the hydroxymethyl radical, the 2-hydroxyethyl radical and the 3-hydroxypropyl radical.

Halogen within the meaning of the invention is bromine, chlorine or fluorine.

2–4C-Alkenyl represents straight-chain or branched alkenyl radicals having 2 to 4 carbon atoms. Examples which may be mentioned are the 2-butenyl radical, 3-butenyl radical, 1-propenyl radical and the 2-propenyl radical (allyl radical).

2–4C-Alkynyl represents straight-chain or branched alkynyl radicals having 2 to 4 carbon atoms. Examples which may be mentioned are the 2-butynyl radical, 3-butynyl radical and preferably the 2-propynyl radical (propargyl radical).

1–4C-Alkoxy represents radicals which, in addition to the oxygen atom, contain a straight-chain or branched alkyl radical having 1 to 4 carbon atoms, Examples which may be mentioned are the butoxy radical, isobutoxy radical, sec-butoxy radical, tert-butoxy radical, propoxy radical, isopropoxy radical and preferably the ethoxy radical and methoxy radical.

1–4C-alkoxy-1–4C-alkyl represents one of the abovementioned 1–4C-alkyl radicals which is substituted by one of the abovementioned 1–4C-alkoxy radicals. Examples which may be mentioned are the methoxymethyl radical, the methoxyethyl radical and the butoxyethyl radical.

Fluoro-1–4C-alkoxy-1–4C-alkyl represents one of the abovementioned 1–4C-alkyl radicals which is substituted by a fluoro-1–4C-alkoxy radical. Fluoro-1–4C-alkoxy in this case represents one of the abovementioned 1–4C-alkoxy radicals which is completely or partly substituted by fluorine. Examples of 1–4C-alkoxy completely or partly substituted by fluorine which may be mentioned are the 1,1,1,3, 3,3-hexafluoro-2-propoxy radical, the 2-trifluormethyl-2-propoxy radical, the 1,1,1-trifluoro-2-propoxy radical, the perfluoro-tert-butoxy radical, the 2,2,3,3,4,4,4-heptafluoro-1-butoxy radical, the 4,4,4-trifluoro-1-butoxy radical, the 2,2,3,3,3-pentafluoropropoxy radical, the perfluoroethoxy radical, the 1,2,2-trifluoroethoxy radical, in particular the 1,1,2,2-tetrafluoroethoxy radical, the 2,2,2-trifluoroethoxy radical, thetrifluormethoxy radical and preferably the difluoromethoxy radical.

1–4C-Alkoxy-1–4C-alkoxy represents one of the abovementioned 1–4C-alkoxy radicals which is substituted by a further 1–4C-alkoxy radical. Examples which may be mentioned are the radicals 2-(methoxy)ethoxy ($CH_3$—O—$CH_2$—$CH_2$—O—) and 2-(ethoxy)ethoxy ($CH_3$—$CH_2$—O—$CH_2$—$CH_2$—O—).

1–4C-Alkylcarbonyl represents a radical which, in addition to the carbonyl group, contains one of the abovementioned 1–4C-alkyl radicals. An example which may be mentioned is the acetyl radical.

1–4C-Alkylcarbonyloxy represents a 1–4C-alkylcarbonyl group which is bonded to an oxygen atom. An example which may be mentioned is the acetoxy radical ($CH_3CO$—O—).

A radical from which a hydroxyl group is formed under physiological conditions is understood as meaning a radical —OR', from which the group R' is removed hydrolytically in the human or animal body with formation of the radical —OH and the nontoxic compound R'OH. The radical R' can thus also be designated as a hydroxy protective group or as a "prodrug" radical. Such hydroxy protective groups or "prodrug" radicals are known, inter alia, from the patent applications and patents DE 4308095, WO 95/14016, EP 694547, WO 95/11884, WO 94/05282 and U.S. Pat. No. 5,432,183. For example, radicals R' having the general structure —C(O)R, —C(O)NRaRb, —P(O)ORaORb or —S(O)$_2$OR can be mentioned, where R, Ra and Rb are any desired organic radicals or optionally hydrogen. In one embodiment of the invention, R4' and R5' have a common hydroxy protective group R', which can then have, for example, one of the structures —CRaRb-, —CRa(ORb)-, —C(ORa)(ORb)- or —P(O)OR—.

1–4C-Alkoxycarbonyl represents a carbonyl group to which one of the above-mentioned 1–4C-alkoxy radicals is bonded. Examples which may be mentioned are the methoxycarbonyl radical ($CH_3O$—C(O)—) and the ethoxycarbonyl radical ($CH_3CH_2O$—C(O)—).

1–4C-Alkoxycarbonylamino represents an amino radical which is substituted by one of the abovementioned 1–4C-alkoxycarbonyl radicals. Examples which may be mentioned are the ethoxycarbonylamino radical and the methoxycarbonylamino radical.

1–4C-Alkoxy-1–4C-alkoxycarbonyl represents a carbonyl group to which one of the abovementioned 1–4C-alkoxy-1–4C-alkoxy radicals is bonded. Examples which may be mentioned are the 2-(methoxy)ethoxycarbonyl radical ($CH_3$—O—$CH_2CH_2$—O—CO—) and the 2-(ethoxy)ethoxycarbonyl radical ($CH_3CH_2$—O—$CH_2CH_2$—O—CO—).

1–4C-Alkoxy-1–4C-alkoxycarbonylamino represents an amino radical which is substituted by one of the abovementioned 1–4C-alkoxy-1–4C-alkoxycarbonyl radicals. Examples which may be mentioned are the 2-(methoxy)ethoxycarbonylamino radical and the 2-(ethoxy)ethoxycarbonylamino radical.

Radicals R' to be mentioned in the context of the invention are the groups to be emphasized by way of example —C(O)—NR8R9,
—C(O)-alk-NR8R9,
—C(O)-alk-C(O)—NR8R9,
—P(O)(OH)$_2$,
—S(O)$_2$NR8R9,
—C(O)—R8,
—C(O)—$C_6H_3$R10R11,
—C(O)—OR8,
—C(O)-alk-C(O)—R8,
—C(O)-alk-C(O)—OR8,
—C(O)—C(O)—R8,
—C(O)—C(O)—OR8 and
—$CH_2$—OR8, where
alk is 1–7C-alkylene,
R8 is hydrogen, 1–10C-alkyl or 1–4C-alkyl substituted by halogen, carboxyl, hydroxyl, sulfo (—$SO_3H$), sulfamoyl (—$SO_2NH_2$), carbamoyl (—$CONH_2$), 1–4C-alkoxy or 1–4C-alkoxycarbonyl,
R9 is hydrogen or 1–4C-alkyl,
R10 is hydrogen, halogen, nitro, 1–4C-alkyl, 1–4C-alkoxy, 1–4C-alkoxycarbonyl, 1–4C-alkoxycarbonylamino, 1–4C-alkoxy-1–4C-alkoxycarbonylamino or trifluormethyl and
R11 is hydrogen, halogen, 1–4C-alkyl or 1–4C-alkoxy.

1–7C-Alkylene represents straight-chain or branched 1–7C-alkylene radicals, for example the methylene radical (—$CH_2$—), ethylene radical. (—$CH_2CH_2$—), trimethylene radical (—$CH_2CH_2CH_2$—), tetramethylene radical (—$CH_2CH_2CH_2CH_2$—), 1,2-dimethylethylene radical [—$CH(CH_3)$—$CH(CH_3)_2$—], 1,1-dimethylethylene radical [—$C(CH_3)_2$—$CH_2$—]2,2-dimethylethylene radical [—$CH_2$—$C(CH_3)_2$—], isopropylidene radical [—$C(CH_3)_2$—], 1-methylethylene radical [—$CH(CH_3)$—$CH_2$—], pentamethylene radical (—$CH_2CH_2CH_2CH_2CH_2$—), hexamethylene radical (—$CH_2CH_2CH_2CH_2CH_2CH_2$—) and the heptamethylene radical (—$CH_2CH_2CH_2CH_2CH_2CH_2CH_2$—).

1–10C-Alkyl within the meaning of the present invention represents straight-chain, branched or cyclic alkyl radicals having 1 to 10 carbon atoms. Examples which may be mentioned are the menthyl radical, neomenthyl radical, isomenthyl radical, neoisomenthyl radical, octyl radical, isooctyl radical (6-methylheptyl radical), heptyl radical, isoheptyl radical (5-methylhexyl radical), hexyl radical, isohexyl radical (4-methylpentyl radical), neohexyl radical (3,3-dimethylbutyl radical), pentyl radical, isopentyl radical (3-methylbutyl radical), neopentyl radical (2,2-dimethylpropyl radical), butyl radical, isobutyl radical, sec-butyl radical, tert-butyl radical, propyl radical, isopropyl radical, ethyl radical and the methyl radical.

In this connection, radicals R' to be mentioned as particularly to be emphasized by way of example are the groups —C(O)—N($CH_3$)$_2$, —C(O)—N($C_2H_5$)$_2$, —C(O)—NH$C_2H_5$, —C(O)—$CH_2CH_2NH_2$, —C(O)—($CH_2$)$_3NH_2$, —C(O)—C($CH_3$)$_2NH_2$, —C(O)—$CH_2N(CH_3)_2$, —C(O)—CH($NH_2$)—CH($CH_3$)$_2$, —C(O)—CH($NH_2$)CH($CH_3$)$C_2H_5$, —C(O)—($CH_2$)$_6$C(O)N($CH_3$)$CH_2CH_2SO_3H$,—P(O)(OH)$_2$, —S(O)$_2NH_2$, —C(O)—H, —C(O)—C($CH_3$)$_3$, —C(O)—$CH_2CH_2COOH$, —C(O)—$CH_3$, —C(O)—$C_2H_5$, —C(O)—$C_6H_5$, —C(O)—$C_6H_4$-4-$NO_2$, —C(O)—$C_6H_4$-3-$NO_2$, —C(O)—$C_6H_4$-4-$OCH_3$, —C(O)—$C_6H_4$-4-C(O)—$OCH_3$, —C(O)—$OCH_3$, —C(O)—O-menthyl, —C(O)—$CH_2$—C(O)—$OCH_3$, —C(O)—$CH_2CH_2$—C(O)—$OCH_3$, —C(O)—C(O)—$OCH_3$, —C(O)—C(O)—$OC_2H_5$ and —$CH_2OCH(CH_3)_2$, or (if R4' and R5' have a common hydroxy protective group) the groups —C(CH$_3$)$_2$—, —P(O)(OH)— and —CH[C(CH$_3$)$_3$]—.

Possible salts of compounds of the formula 1—depending on substitution—are especially all acid addition salts. Particular mention may be made of the pharmacologically tolerable salts of the inorganic and organic acids customarily used in pharmacy. Those suitable are water-soluble and water-insoluble acid addition salts with acids such as hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, where the acids are employed in salt preparation—depending on whether a mono- or polybasic acid is concerned and depending on which salt is desired—in an equimolar quantitative ratio or one differing therefrom.

Pharmacologically intolerable salts which can be initially obtained, for example, as process products in the preparation of the compounds according to the invention on an industrial scale, are converted into pharmacologically tolerable salts by processes known to the person skilled in the art.

It is known to the person skilled in the art that the compounds according to the invention and their salts, if they are isolated, for example, in crystalline form, can contain various amounts of solvents. The invention therefore also comprises all solvates and in particular all hydrates of the compounds of the formula 1, and also all solvates and in particular all hydrates of the salts of the compounds of the formula 1.

The compounds of the formula 1 have at least two chiral centers. The invention relates to all conceivable stereoisomers in any desired mixing ratio with one another, including the pure enantiomers, which are a preferred subject of the invention.

One embodiment (embodiment a) of the invention are compounds of the formula 1 in which R3 is hydrogen.

A further embodiment (embodiment b) of the invention are compounds of the formula 1 in which R3 is halogen.

A further embodiment (embodiment c) of the invention are compounds of the formula 1 in which R3 is carboxyl, —CO-1–4C-alkoxy, hydroxy-1–4C-alkyl, 1–4C-alkoxy-1–4C-alkyl, fluoro-1–4C-alkoxy-1–4C-alkyl or the radical —CO—NR3aR3b.

A preferred radical R1 by way of example is the methyl radical.

Preferred radicals R2 by way of example are the hydroxymethyl radical and in particular the methyl radical.

R3 in the context of the present invention is preferably hydrogen, halogen, carboxyl, —CO-1–4C-alkoxy, hydroxy-1–4C-alkyl, 1–4C-alkoxy-1–4C-alkyl, fluoro-1–4C-alkoxy-1–4C-alkyl or the radical —CO—NR3aR3b.

Particularly worthy of mention in the context of the present invention are compounds of the formula 1, in which R1 is 1–4C-alkyl, R2 is 1–4C-alkyl or hydroxy-1–4C-alkyl, R3 is hydrogen, halogen, carboxyl, —CO-1–4C-alkoxy, hydroxy-1–4C-alkyl, 1–4C-alkoxy-1–4C-alkyl, fluoro-1–4C-alkoxy-1–4C-alkyl or the radical —CO—NR3aR3b, one of the substituents R4a and R4b is hydrogen and the other is hydroxyl, 1–4C-alkoxy, 1–4C-alkoxy-1–4C-alkoxy or the radical —OR', or in which R4a and R4b together are O (oxygen), one of the substituents R5a and R5b is hydrogen and the other is hydrogen, hydroxyl, 1–4C-alkoxy, 1–4C-alkoxy-1–4C-alkoxy or the radical —OR', or in which R5a and R5b together are O (oxygen), where one of the substituents R4a and R4b must have the meaning —OR' and/or one of the substituents R5a and R5b must have the meaning —OR', R6 is hydrogen, halogen, 1–4C-alkyl, 1–4C-alkoxy, 1–4C-alkoxycarbonylamino, 1–4C-alkoxy-1–4C-alkoxycarbonylamino or trifluoromethyl, R7 is hydrogen, halogen, 1–4C-alkyl or 1–4C-alkoxy and X is O (oxygen) or NH, where R3a is hydrogen, 1–7C-alkyl, hydroxy-1–4C-alkyl or 1–4C-alkoxy-1–4C-alkyl and R3b is hydrogen, 1–7C-alkyl, hydroxy-1–4C-alkyl or 1–4C-alkoxy-1–4C-alkyl, or where R3a and R3b together, including the nitrogen atom to which both are bonded, are a pyrrolidino, piperidino or morpholino radical, and where R' is selected from the group consisting of

—C(O)—NR8R9,

—C(O)-alk-NR8R9,

—C(O)-alk-C(O)—NR8R9,

—P(O)(OH)$_2$,

—S(O)$_2$NR8R9,

—C(O)—R8,

—C(O)—C$_6$H$_3$R10R11,

—C(O)—OR8,

—C(O)-alk-C(O)—R8,

—C(O)-alk-C(O)—OR8,

—C(O)—C(O)—R8,

—C(O)—C(O)—OR8 and

—CH$_2$—OR8, where alk is 1–7C-alkylene,

R8 is hydrogen, 1–10C-alkyl or 1–4C-alkyl substituted by halogen, carboxyl, hydroxyl, sulfo (—SO$_3$H), sulfamoyl (—SO$_2$NH$_2$), carbamoyl (—CONH$_2$), 1–4C-alkoxy or 1–4C-alkoxycarbonyl, R9 is hydrogen or 1–4C-alkyl, R10 is hydrogen, halogen, nitro, 1–4C-alkyl, 1–4C-alkoxy, 1–4C-alkoxycarbonyl, 1–4C-alkoxycarbonylamino, 1–4C-alkoxy-1–4C-alkoxycarbonylamino or trifluoromethyl and R11 is hydrogen, halogen, 1–4C-alkyl or 1–4C-alkoxy, and the salts of the compounds.

Compounds of the invention to be emphasized are those of the formula 1*,

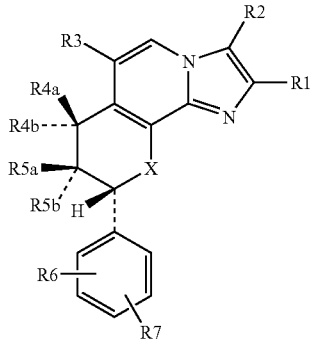

in which
R1 is 1–4C-alkyl,
R2 is 1–4C-alkyl,
R3 is hydrogen, chlorine, fluorine, hydroxymethyl, difluoromethoxymethyl or the radical —CO—NR3aR3b,
one of the substituents R4a and R4b is hydrogen and the other is hydroxyl, 1–4C-alkoxy, 1–4C-alkoxy-1–4C-alkoxy or the radical —OR', or in which R4a and R4b together are O (oxygen), one of the substituents R5a and R5b is hydrogen and the other is hydroxyl, 1–4C-alkoxy, 1–4C-alkoxy-1–4C-alkoxy or the radical —OR', or in which R5a and R5b together are O (oxygen), where one of the substituents R4a and R4b must have the meaning —OR' and/or one of the substituents R5a and R5b must have the meaning —OR',
R6 is hydrogen,
R7 is hydrogen and
X is O (oxygen) or NH, where
R3a is hydrogen, 1–4C-alkyl, hydroxy-1–4C-alkyl or 1–4C-alkoxy-1–4C-alkyl and
R3b is hydrogen, 1–4C-alkyl, hydroxy-1–4C-alkyl or 1–4C-alkoxy-1–4C-alkyl, and where
R' is selected from the group consisting of
—C(O)—NR8R9,
—C(O)-alk-NR8R9,
—C(O)-alk-C(O)—NR8R9,
—P(O)(OH)$_2$,
—S(O)$_2$NR8R9,
—C(O)—R8,
—C(O)—C$_6$H$_3$R10R11,
—C(O)—OR8,
—C(O)-alk-C(O)—OR8,
—C(O)—C(O)—OR8 and
—CH$_2$—OR8, where
alk is 1–7C-alkylene,
R8 is hydrogen, 1–10C-alkyl or 1–4C-alkyl substituted by carboxyl or sulfo (—SO$_3$H),
R9 is hydrogen or 1–4C-alkyl,
R10 is hydrogen, halogen, nitro, 1–4-C-alkyl, 1–4C-alkoxy, 1–4C-alkoxycarbonyl, 1–4C-alkoxycarbonylamino, 1–4C-alkoxy-1–4C-alkoxycarbonylamino or trifluormethyl and
R11 is hydrogen, halogen, 1–4C-alkyl or 1–4C-alkoxy, and the salts of the compounds.

Compounds of the invention particularly to be emphasized are those of the formula 1*, in which
R1' is methyl,
R2 is methyl,
R3 is hydrogen, chlorine, fluorine, hydroxymethyl, difluoromethoxymethyl or the radical —CO—NR3aR3b,
one of the substituents R4a and R4b is hydrogen and the other is 1–4C-alkoxy or 1–4C-alkoxy-1–4C-alkoxy,
one of the substituents R5a and R5b is hydrogen and the other is the radical —OR',
R6 is hydrogen,
R7 is hydrogen and
X is O (oxygen) or NH, where
R3a is hydrogen, methyl, ethyl, propyl, 2-hydroxyethyl or 2-methoxyethyl and
R3b is hydrogen, methyl or ethyl, and where
R' is selected from the group consisting of
—C(O)—NR8R9,
—C(O)-alk-NR8R9,
—C(O)-alk-C(O)—NR8R9,
—P(O)(OH)$_2$,
—S(O)$_2$NR8R9,
—C(O)—R8,
—C(O)—C$_6$H$_3$R10R11,
—C(O)—OR8,
—C(O)-alk-C(O)—OR8,
—C(O)—C(O)—OR8 and
—CH$_2$—OR8, where
alk is 1–7C-alkylene,
R8 is hydrogen, 1–10C-alkyl or 1–4C-alkyl substituted by carboxyl or sulfo (—SO$_3$H),
R9 is hydrogen or 1–4C-alkyl,
R10 is hydrogen, halogen, nitro, 1–4C-alkyl, 1–4C-alkoxy, 1–4C-alkoxycarbonyl- or trifluoro-methyl and
R11 is hydrogen or halogen, and the salts of the compounds.

Compounds of the formula 1 to be particularly emphasized by way of example are those in which R' has the meaning —C(O)—N(CH$_3$)$_2$, —C(O)—N(C$_2$H$_5$)$_2$, —C(O)—NHC$_2$H$_5$, —C(O)—CH$_2$CH$_2$NH$_2$, —C(O)—(CH$_2$)$_3$NH$_2$, —C(O)—C(CH$_3$)$_2$NH$_2$, —C(O)—CH$_2$N(CH$_3$)$_2$, —C(O)—CH(NH$_2$)—CH(CH$_3$)$_2$, —C(O)—CH(NH$_2$)CH(CH$_3$)C$_2$H$_5$, —C(O)—(CH$_2$)$_6$C(O)N(CH$_3$)CH$_2$CH$_2$SO$_3$H, —P(O)(OH)$_2$, —S(O)$_2$NH$_2$, —C(O)—H, —C(O)—C(CH$_3$)$_3$, —C(O)—CH$_2$CH$_2$COOH, —C(O)—CH$_3$, —C(O)—C$_2$H$_5$, —C(O)—C$_6$H$_5$, —C(O)—C$_6$H$_4$-4-NO$_2$, —C(O)—C$_6$H$_4$-3-NO$_2$, —C(O)—C$_6$H$_{44}$—OCH$_3$, —C(O)—C$_6$H$_{44}$—C(O)—OCH$_3$, —C(O)—OCH$_3$, —C(O)—O-menthyl, —C(O)—CH$_2$—C(O)—OCH$_3$, —C(O)—CH$_2$CH$_2$—C(O)—OCH$_3$, —C(O)—C(O)—OCH$_3$, —C(O)—C(O)—OC$_2$H$_5$ or —CH$_2$OCH(CH$_3$)$_2$.

Preferred compounds of the invention are those of the formula 1*, in which
R1 is methyl,
R2 is methyl,
R3 is hydrogen, chlorine, fluorine, hydroxymethyl, difluoromethoxymethyl or the radical —CO—NR3aR3b,
one of the substituents R4a and R4b is hydrogen and the other is 1–4C-alkoxy or 1–4C-alkoxy-1–4C-alkoxy,
R5a is the radical —OR', R5b is hydrogen,
R6 is hydrogen,
R7 is hydrogen and
X is O (oxygen) or NH, where
R3a is hydrogen, methyl, ethyl, propyl, 2-hydroxyethyl or 2-methoxyethyl and
R3b is hydrogen, methyl or ethyl, and where
R' is selected from the group consisting of
—C(O)—NR8R9,
—C(O)-alk-NR8R9,
—C(O)—R8
—C(O)—$C_6H_3R10R11$,
—C(O)—OR8,
—C(O)-alk-C(O)-9R8, and
—C(O)—C(O)—OR8, where
alk is 1–4C-alkylene,
R8 is hydrogen, 1–4C-alkyl or menthyl,
R9 is hydrogen or 1–4C-alkyl,
R10 is hydrogen, halogen, nitro, 1–4C-alkyl, 1–4C-alkoxy, 1–4C-alkoxycarbonyl or trifluoro-methyl and
R11 is hydrogen or halogen, and the salts of the compounds.

In the Examples below, the absolute configuration "R" for both positions 8 and 9 has been assigned to these preferred compounds of formula 1* in which R5a is the radical —OR' and R5b is hydrogen.

Preferred compounds of embodiment a of the invention are those of the formula 1* in which R3 is hydrogen.

Preferred compounds of embodiment b of the invention are those of the formula 1* in which R3 is chlorine or fluorine.

Preferred compounds of embodiment c of the invention are those of the formula 1* in which R3 is hydroxymethyl, difluoromethoxymethyl or the radical —CO—NR3aR3b.

The following exemplary preferred compounds according to the invention may be mentioned in actual terms with the aid of the general formula 1*, in which R1 is methyl, R2 is methyl, R5b is hydrogen, R6 is hydrogen and R7 is hydrogen, by the substituent meanings for R3, R4a, R4b, R5a and X in the table 1 (Tab. 1) below (Ph is phenyl):

TABLE 1

| R3 | R4a | R4b | R5a | X |
|---|---|---|---|---|
| H | H | $CH_3O$ | $CH_3COO$ | NH |
| H | H | $CH_3OCH_2CH_2O$ | $CH_3COO$ | NH |
| H | H | $CH_3O$ | $(CH_3)_3CCOO$ | NH |
| H | H | $CH_3OCH_2CH_2O$ | $(CH_3)_3CCOO$ | NH |
| H | H | $CH_3O$ | PhCOO | NH |
| H | H | $CH_3OCH_2CH_2O$ | PhCOO | NH |
| H | H | $CH_3O$ | $(C_2H_5)_2NCOO$ | NH |
| H | H | $CH_3OCH_2CH_2O$ | $(C_2H_5)_2NCOO$ | NH |
| H | H | $CH_3O$ | $CH_3OCOO$ | NH |
| H | H | $CH_3OCH_2CH_2O$ | $CH_3OCOO$ | NH |
| H | H | $CH_3O$ | $(CH_3)_2NCH_2COO$ | NH |
| H | H | $CH_3OCH_2CH_2O$ | $(CH_3)_2NCH_2COO$ | NH |
| H | H | $CH_3O$ | $CH_3OCOCH_2CH_2COO$ | NH |
| H | H | $CH_3OCH_2CH_2O$ | $CH_3OCOCH_2CH_2COO$ | NH |
| Cl | H | $CH_3O$ | $CH_3COO$ | NH |
| Cl | H | $CH_3OCH_2CH_2O$ | $CH_3COO$ | NH |
| Cl | H | $CH_3O$ | $(CH_3)_3CCOO$ | NH |
| Cl | H | $CH_3OCH_2CH_2O$ | $(CH_3)_3CCOO$ | NH |
| Cl | H | $CH_3O$ | PhCOO | NH |
| Cl | H | $CH_3OCH_2CH_2O$ | PhCOO | NH |
| Cl | H | $CH_3O$ | $(C_2H_5)_2NCOO$ | NH |
| Cl | H | $CH_3OCH_2CH_2O$ | $(C_2H_5)_2NCOO$ | NH |
| Cl | H | $CH_3O$ | $CH_3OCOO$ | NH |
| Cl | H | $CH_3OCH_2CH_2O$ | $CH_3OCOO$ | NH |
| Cl | H | $CH_3O$ | $(CH_3)_2NCH_2COO$ | NH |
| Cl | H | $CH_3OCH_2CH_2O$ | $(CH_3)_2NCH_2COO$ | NH |
| Cl | H | $CH_3O$ | $CH_3OCOCH_2CH_2COO$ | NH |
| Cl | H | $CH_3OCH_2CH_2O$ | $CH_3OCOCH_2CH_2COO$ | NH |
| F | H | $CH_3O$ | $CH_3COO$ | NH |
| F | H | $CH_3OCH_2CH_2O$ | $CH_3COO$ | NH |
| F | H | $CH_3O$ | $(CH_3)_3CCOO$ | NH |
| F | H | $CH_3OCH_2CH_2O$ | $(CH_3)_3CCOO$ | NH |
| F | H | $CH_3O$ | PhCOO | NH |
| F | H | $CH_3OCH_2CH_2O$ | PhCOO | NH |
| F | H | $CH_3O$ | $(C_2H_5)_2NCOO$ | NH |
| F | H | $CH_3OCH_2CH_2O$ | $(C_2H_5)_2NCOO$ | NH |
| F | H | $CH_3O$ | $CH_3OCOO$ | NH |
| F | H | $CH_3OCH_2CH_2O$ | $CH_3OCOO$ | NH |
| F | H | $CH_3O$ | $(CH_3)_2NCH_2COO$ | NH |
| F | H | $CH_3OCH_2CH_2O$ | $(CH_3)_2NCH_2COO$ | NH |
| F | H | $CH_3O$ | $CH_3OCOCH_2CH_2COO$ | NH |
| F | H | $CH_3OCH_2CH_2O$ | $CH_3OCOCH_2CH_2COO$ | NH |
| $HOCH_2$ | H | $CH_3O$ | $CH_3COO$ | NH |
| $HOCH_2$ | H | $CH_3OCH_2CH_2O$ | $CH_3COO$ | NH |
| $HOCH_2$ | H | $CH_3O$ | $(CH_3)_3CCOO$ | NH |
| $HOCH_2$ | H | $CH_3OCH_2CH_2O$ | $(CH_3)_3CCOO$ | NH |
| $HOCH_2$ | H | $CH_3O$ | PhCOO | NH |
| $HOCH_2$ | H | $CH_3OCH_2CH_2O$ | PhCOO | NH |

TABLE 1-continued

| R3 | R4a | R4b | R5a | X |
| --- | --- | --- | --- | --- |
| HOCH$_2$ | H | CH$_3$O | (C$_2$H$_5$)$_2$NCOO | NH |
| HOCH$_2$ | H | CH$_3$OCH$_2$CH$_2$O | (C$_2$H$_5$)$_2$NCOO | NH |
| HOCH$_2$ | H | CH$_3$O | CH$_3$OCOO | NH |
| HOCH$_2$ | H | CH$_3$OCH$_2$CH$_2$O | CH$_3$OCOO | NH |
| HOCH$_2$ | H | CH$_3$O | (CH$_3$)$_2$NCH$_2$COO | NH |
| HOCH$_2$ | H | CH$_3$OCH$_2$CH$_2$O | (CH$_3$)$_2$NCH$_2$COO | NH |
| HOCH$_2$ | H | CH$_3$O | CH$_3$OCOCH$_2$CH$_2$COO | NH |
| HOCH$_2$ | H | CH$_3$OCH$_2$CH$_2$O | CH$_3$OCOCH$_2$CH$_2$COO | NH |
| CHF$_2$OCH$_2$ | H | CH$_3$O | CH$_3$COO | NH |
| CHF$_2$OCH$_2$ | H | CH$_3$OCH$_2$CH$_2$O | CH$_3$COO | NH |
| CHF$_2$OCH$_2$ | H | CH$_3$O | (CH$_3$)$_3$CCOO | NH |
| CHF$_2$OCH$_2$ | H | CH$_3$OCH$_2$CH$_2$O | (CH$_3$)$_3$CCOO | NH |
| CHF$_2$OCH$_2$ | H | CH$_3$O | PhCOO | NH |
| CHF$_2$OCH$_2$ | H | CH$_3$OCH$_2$CH$_2$O | PhCOO | NH |
| CHF$_2$OCH$_2$ | H | CH$_3$O | (C$_2$H$_5$)$_2$NCOO | NH |
| CHF$_2$OCH$_2$ | H | CH$_3$OCH$_2$CH$_2$O | (C$_2$H$_5$)$_2$NCOO | NH |
| CHF$_2$OCH$_2$ | H | CH$_3$O | CH$_3$OCOO | NH |
| CHF$_2$OCH$_2$ | H | CH$_3$OCH$_2$CH$_2$O | CH$_3$OCOO | NH |
| CHF$_2$OCH$_2$ | H | CH$_3$O | (CH$_3$)$_2$NCH$_2$COO | NH |
| CHF$_2$OCH$_2$ | H | CH$_3$OCH$_2$CH$_2$O | (CH$_3$)$_2$NCH$_2$COO | NH |
| CHF$_2$OCH$_2$ | H | CH$_3$O | CH$_3$OCOCH$_2$CH$_2$COO | NH |
| CHF$_2$OCH$_2$ | H | CH$_3$OCH$_2$CH$_2$O | CH$_3$OCOCH$_2$CH$_2$COO | NH |
| (HOCH$_2$CH$_2$)NHCO | H | CH$_3$O | CH$_3$COO | NH |
| (HOCH$_2$CH$_2$)NHCO | H | CH$_3$OCH$_2$CH$_2$O | CH$_3$COO | NH |
| (HOCH$_2$CH$_2$)NHCO | H | CH$_3$O | (CH$_3$)$_3$CCOO | NH |
| (HOCH$_2$CH$_2$)NHCO | H | CH$_3$OCH$_2$CH$_2$O | (CH$_3$)$_3$CCOO | NH |
| (HOCH$_2$CH$_2$)NHCO | H | CH$_3$O | PhCOO | NH |
| (HOCH$_2$CH$_2$)NHCO | H | CH$_3$OCH$_2$CH$_2$O | PhCOO | NH |
| (HOCH$_2$CH$_2$)NHCO | H | CH$_3$O | (C$_2$H$_5$)$_2$NCOO | NH |
| (HOCH$_2$CH$_2$)NHCO | H | CH$_3$OCH$_2$CH$_2$O | (C$_2$H$_5$)$_2$NCOO | NH |
| (HOCH$_2$CH$_2$)NHCO | H | CH$_3$O | CH$_3$OCOO | NH |
| (HOCH$_2$CH$_2$)NHCO | H | CH$_3$OCH$_2$CH$_2$O | CH$_3$OCOO | NH |
| (HOCH$_2$CH$_2$)NHCO | H | CH$_3$O | (CH$_3$)$_2$NCH$_2$COO | NH |
| (HOCH$_2$CH$_2$)NHCO | H | CH$_3$OCH$_2$CH$_2$O | (CH$_3$)$_2$NCH$_2$COO | NH |
| (HOCH$_2$CH$_2$)NHCO | H | CH$_3$O | CH$_3$OCOCH$_2$CH$_2$COO | NH |
| (HOCH$_2$CH$_2$)NHCO | H | CH$_3$OCH$_2$CH$_2$O | CH$_3$OCOCH$_2$CH$_2$COO | NH |
| (CH$_3$OCH$_2$CH$_2$)NHCO | H | CH$_3$O | CH$_3$COO | NH |
| (CH$_3$OCH$_2$CH$_2$)NHCO | H | CH$_3$OCH$_2$CH$_2$O | CH$_3$COO | NH |
| (CH$_3$OCH$_2$CH$_2$)NHCO | H | CH$_3$O | (CH$_3$)$_3$CCOO | NH |
| (CH$_3$OCH$_2$CH$_2$)NHCO | H | CH$_3$OCH$_2$CH$_2$O | (CH$_3$)$_3$CCOO | NH |
| (CH$_3$OCH$_2$CH$_2$)NHCO | H | CH$_3$O | PhCOO | NH |
| (CH$_3$OCH$_2$CH$_2$)NHCO | H | CH$_3$OCH$_2$CH$_2$O | PhCOO | NH |
| (CH$_3$OCH$_2$CH$_2$)NHCO | H | CH$_3$O | (C$_2$H$_5$)$_2$NCOO | NH |
| (CH$_3$OCH$_2$CH$_2$)NHCO | H | CH$_3$OCH$_2$CH$_2$O | (C$_2$H$_5$)$_2$NCOO | NH |
| (CH$_3$OCH$_2$CH$_2$)NHCO | H | CH$_3$O | CH$_3$OCOO | NH |
| (CH$_3$OCH$_2$CH$_2$)NHCO | H | CH$_3$OCH$_2$CH$_2$O | CH$_3$OCOO | NH |
| (CH$_3$OCH$_2$CH$_2$)NHCO | H | CH$_3$O | (CH$_3$)$_2$NCH$_2$COO | NH |
| (CH$_3$OCH$_2$CH$_2$)NHCO | H | CH$_3$OCH$_2$CH$_2$O | (CH$_3$)$_2$NCH$_2$COO | NH |
| (CH$_3$OCH$_2$CH$_2$)NHCO | H | CH$_3$O | CH$_3$OCOCH$_2$CH$_2$COO | NH |
| (CH$_3$OCH$_2$CH$_2$)NHCO | H | CH$_3$OCH$_2$CH$_2$O | CH$_3$OCOCH$_2$CH$_2$COO | NH |
| H | H | CH$_3$O | CH$_3$COO | O |
| H | H | CH$_3$OCH$_2$CH$_2$O | CH$_3$COO | O |
| H | H | CH$_3$O | (CH$_3$)$_3$CCOO | O |
| H | H | CH$_3$OCH$_2$CH$_2$O | (CH$_3$)$_3$CCOO | O |
| H | H | CH$_3$O | PhCOO | O |
| H | H | CH$_3$OCH$_2$CH$_2$O | PhCOO | O |
| H | H | CH$_3$O | (C$_2$H$_5$)$_2$NCOO | O |
| H | H | CH$_3$OCH$_2$CH$_2$O | (C$_2$H$_5$)$_2$NCOO | O |
| H | H | CH$_3$O | CH$_3$OCOO | O |
| H | H | CH$_3$OCH$_2$CH$_2$O | CH$_3$OCOO | O |
| H | H | CH$_3$O | (CH$_3$)$_2$NCH$_2$COO | O |
| H | H | CH$_3$OCH$_2$CH$_2$O | (CH$_3$)$_2$NCH$_2$COO | O |
| H | H | CH$_3$O | CH$_3$OCOCH$_2$CH$_2$COO | O |
| H | H | CH$_3$OCH$_2$CH$_2$O | CH$_3$OCOCH$_2$CH$_2$COO | O |
| Cl | H | CH$_3$O | CH$_3$COO | O |
| Cl | H | CH$_3$OCH$_2$CH$_2$O | CH$_3$COO | O |
| Cl | H | CH$_3$O | (CH$_3$)$_3$CCOO | O |
| Cl | H | CH$_3$OCH$_2$CH$_2$O | (CH$_3$)$_3$CCOO | O |
| Cl | H | CH$_3$O | PhCOO | O |
| Cl | H | CH$_3$OCH$_2$CH$_2$O | PhCOO | O |
| Cl | H | CH$_3$O | (C$_2$H$_5$)$_2$NCOO | O |
| Cl | H | CH$_3$OCH$_2$CH$_2$O | (C$_2$H$_5$)$_2$NCOO | O |
| Cl | H | CH$_3$O | CH$_3$OCOO | O |
| Cl | H | CH$_3$OCH$_2$CH$_2$O | CH$_3$OCOO | O |
| Cl | H | CH$_3$O | (CH$_3$)$_2$NCH$_2$COO | O |
| Cl | H | CH$_3$OCH$_2$CH$_2$O | (CH$_3$)$_2$NCH$_2$COO | O |
| Cl | H | CH$_3$O | CH$_3$OCOCH$_2$CH$_2$COO | O |

TABLE 1-continued

| R3 | R4a | R4b | R5a | X |
|---|---|---|---|---|
| Cl | H | $CH_3OCH_2CH_2O$ | $CH_3OCOCH_2CH_2COO$ | O |
| F | H | $CH_3O$ | $CH_3COO$ | O |
| F | H | $CH_3OCH_2CH_2O$ | $CH_3COO$ | O |
| F | H | $CH_3O$ | $(CH_3)_3CCOO$ | O |
| F | H | $CH_3OCH_2CH_2O$ | $(CH_3)_3CCOO$ | O |
| F | H | $CH_3O$ | $PhCOO$ | O |
| F | H | $CH_3OCH_2CH_2O$ | $PhCOO$ | O |
| F | H | $CH_3O$ | $(C_2H_5)_2NCOO$ | O |
| F | H | $CH_3OCH_2CH_2O$ | $(C_2H_5)_2NCOO$ | O |
| F | H | $CH_3O$ | $CH_3OCOO$ | O |
| F | H | $CH_3OCH_2CH_2O$ | $CH_3OCOO$ | O |
| F | H | $CH_3O$ | $(CH_3)_2NCH_2COO$ | O |
| F | H | $CH_3OCH_2CH_2O$ | $(CH_3)_2NCH_2COO$ | O |
| F | H | $CH_3O$ | $CH_3OCOCH_2CH_2COO$ | O |
| F | H | $CH_3OCH_2CH_2O$ | $CH_3OCOCH_2CH_2COO$ | O |
| $HOCH_2$ | H | $CH_3O$ | $CH_3COO$ | O |
| $HOCH_2$ | H | $CH_3OCH_2CH_2O$ | $CH_3COO$ | O |
| $HOCH_2$ | H | $CH_3O$ | $(CH_3)_3CCOO$ | O |
| $HOCH_2$ | H | $CH_3OCH_2CH_2O$ | $(CH_3)_3CCOO$ | O |
| $HOCH_2$ | H | $CH_3O$ | $PhCOO$ | O |
| $HOCH_2$ | H | $CH_3OCH_2CH_2O$ | $PhCOO$ | O |
| $HOCH_2$ | H | $CH_3O$ | $(C_2H_5)_2NCOO$ | O |
| $HOCH_2$ | H | $CH_3OCH_2CH_2O$ | $(C_2H_5)_2NCOO$ | O |
| $HOCH_2$ | H | $CH_3O$ | $CH_3OCOO$ | O |
| $HOCH_2$ | H | $CH_3OCH_2CH_2O$ | $CH_3OCOO$ | O |
| $HOCH_2$ | H | $CH_3O$ | $(CH_3)_2NCH_2COO$ | O |
| $HOCH_2$ | H | $CH_3OCH_2CH_2O$ | $(CH_3)_2NCH_2COO$ | O |
| $HOCH_2$ | H | $CH_3O$ | $CH_3OCOCH_2CH_2COO$ | O |
| $HOCH_2$ | H | $CH_3OCH_2CH_2O$ | $CH_3OCOCH_2CH_2COO$ | O |
| $CHF_2OCH_2$ | H | $CH_3O$ | $CH_3COO$ | O |
| $CHF_2OCH_2$ | H | $CH_3OCH_2CH_2O$ | $CH_3COO$ | O |
| $CHF_2OCH_2$ | H | $CH_3O$ | $(CH_3)_3CCOO$ | O |
| $CHF_2OCH_2$ | H | $CH_3OCH_2CH_2O$ | $(CH_3)_3CCOO$ | O |
| $CHF_2OCH_2$ | H | $CH_3O$ | $PhCOO$ | O |
| $CHF_2OCH_2$ | H | $CH_3OCH_2CH_2O$ | $PhCOO$ | O |
| $CHF_2OCH_2$ | H | $CH_3O$ | $(C_2H_5)_2NCOO$ | O |
| $CHF_2OCH_2$ | H | $CH_3OCH_2CH_2O$ | $(C_2H_5)_2NCOO$ | O |
| $CHF_2OCH_2$ | H | $CH_3O$ | $CH_3OCOO$ | O |
| $CHF_2OCH_2$ | H | $CH_3OCH_2CH_2O$ | $CH_3OCOO$ | O |
| $CHF_2OCH_2$ | H | $CH_3O$ | $(CH_3)_2NCH_2COO$ | O |
| $CHF_2OCH_2$ | H | $CH_3OCH_2CH_2O$ | $(CH_3)_2NCH_2COO$ | O |
| $CHF_2OCH_2$ | H | $CH_3O$ | $CH_3OCOCH_2CH_2COO$ | O |
| $CHF_2OCH_2$ | H | $CH_3OCH_2CH_2O$ | $CH_3OCOCH_2CH_2COO$ | O |
| $(HOCH_2CH_2)NHCO$ | H | $CH_3O$ | $CH_3COO$ | O |
| $(HOCH_2CH_2)NHCO$ | H | $CH_3OCH_2CH_2O$ | $CH_3COO$ | O |
| $(HOCH_2CH_2)NHCO$ | H | $CH_3O$ | $(CH_3)_3CCOO$ | O |
| $(HOCH_2CH_2)NHCO$ | H | $CH_3OCH_2CH_2O$ | $(CH_3)_3CCOO$ | O |
| $(HOCH_2CH_2)NHCO$ | H | $CH_3O$ | $PhCOO$ | O |
| $(HOCH_2CH_2)NHCO$ | H | $CH_3OCH_2CH_2O$ | $PhCOO$ | O |
| $(HOCH_2CH_2)NHCO$ | H | $CH_3O$ | $(C_2H_5)_2NCOO$ | O |
| $(HOCH_2CH_2)NHCO$ | H | $CH_3OCH_2CH_2O$ | $(C_2H_5)_2NCOO$ | O |
| $(HOCH_2CH_2)NHCO$ | H | $CH_3O$ | $CH_3OCOO$ | O |
| $(HOCH_2CH_2)NHCO$ | H | $CH_3OCH_2CH_2O$ | $CH_3OCOO$ | O |
| $(HOCH_2CH_2)NHCO$ | H | $CH_3O$ | $(CH_3)_2NCH_2COO$ | O |
| $(HOCH_2CH_2)NHCO$ | H | $CH_3OCH_2CH_2O$ | $(CH_3)_2NCH_2COO$ | O |
| $(HOCH_2CH_2)NHCO$ | H | $CH_3O$ | $CH_3OCOCH_2CH_2COO$ | O |
| $(HOCH_2CH_2)NHCO$ | H | $CH_3OCH_2CH_2O$ | $CH_3OCOCH_2CH_2COO$ | O |
| $(CH_3OCH_2CH_2)NHCO$ | H | $CH_3O$ | $CH_3COO$ | O |
| $(CH_3OCH_2CH_2)NHCO$ | H | $CH_3OCH_2CH_2O$ | $CH_3COO$ | O |
| $(CH_3OCH_2CH_2)NHCO$ | H | $CH_3O$ | $(CH_3)_3CCOO$ | O |
| $(CH_3OCH_2CH_2)NHCO$ | H | $CH_3OCH_2CH_2O$ | $(CH_3)_3CCOO$ | O |
| $(CH_3OCH_2CH_2)NHCO$ | H | $CH_3O$ | $PhCOO$ | O |
| $(CH_3OCH_2CH_2)NHCO$ | H | $CH_3OCH_2CH_2O$ | $PhCOO$ | O |
| $(CH_3OCH_2CH_2)NHCO$ | H | $CH_3O$ | $(C_2H_5)_2NCOO$ | O |
| $(CH_3OCH_2CH_2)NHCO$ | H | $CH_3OCH_2CH_2O$ | $(C_2H_5)_2NCOO$ | O |
| $(CH_3OCH_2CH_2)NHCO$ | H | $CH_3O$ | $CH_3OCOO$ | O |
| $(CH_3OCH_2CH_2)NHCO$ | H | $CH_3OCH_2CH_2O$ | $CH_3OCOO$ | O |
| $(CH_3OCH_2CH_2)NHCO$ | H | $CH_3O$ | $(CH_3)_2NCH_2COO$ | O |
| $(CH_3OCH_2CH_2)NHCO$ | H | $CH_3OCH_2CH_2O$ | $(CH_3)_2NCH_2COO$ | O |
| $(CH_3OCH_2CH_2)NHCO$ | H | $CH_3O$ | $CH_3OCOCH_2CH_2COO$ | O |
| $(CH_3OCH_2CH_2)NHCO$ | H | $CH_3OCH_2CH_2O$ | $CH_3OCOCH_2CH_2COO$ | O | and the salts of these compounds.

The compounds according to the invention can thus be prepared as described by way of example in the following examples, or using analogous process steps starting from corresponding starting compounds (see, for example, WO 98/42707, WO 98/54188, EP-A-299470 or Kaminski et al., J. Med. Chem. 1985, 28, 876–892 and Angew. Chem. 1996, 108, 589–591). The starting compounds are known or they can be prepared in an analogous manner to the known compounds. The compounds according to the invention can be prepared, for example, according to the following reaction schemes.

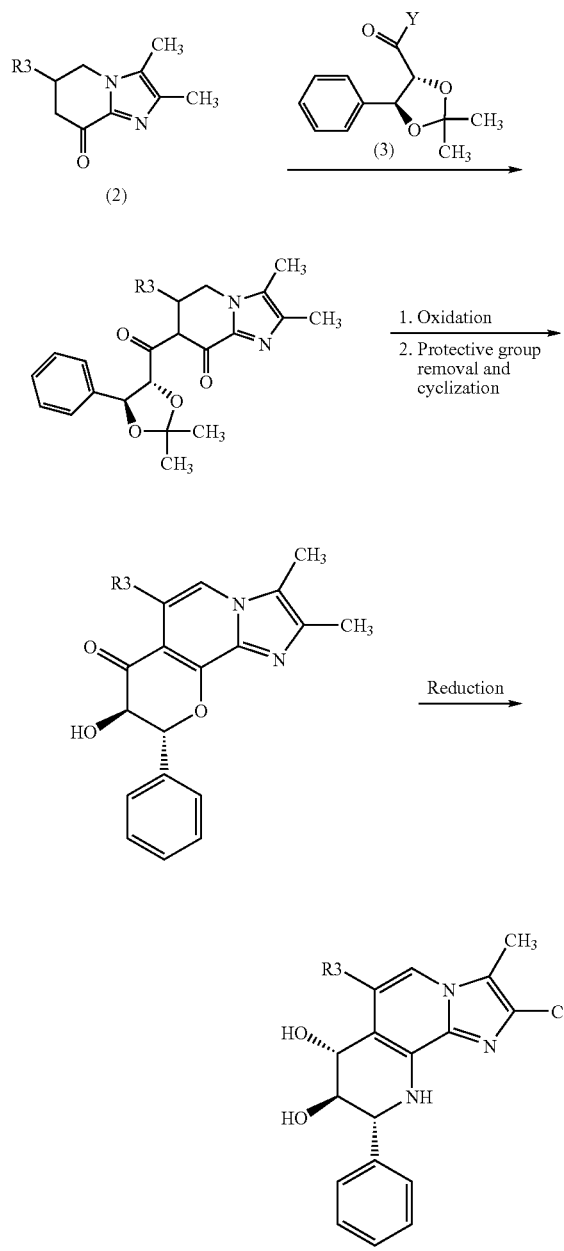

The above scheme 1 shows by way of example the enantioselective synthesis of a 7,8-diol (R4a or R4b and R5a or R5b are in each case hydroxyl) which can then, if desired, be additionally etherified in a suitable manner.

The group Y in the above compound 3 is a suitable leaving group, for example a halogen atom, preferably chlorine. The acylation is carried out in a manner habitual to the person skilled in the art, preferably using bis(trimethylsilyl)sodium amide or potassium amide if the leaving group is a chlorine atom.

The oxidation following the acylation is likewise carried out under conditions customary per se using chloranil, atmospheric oxygen or manganese dioxide as an oxidant. For the subsequent protective group removal and cyclization, certain conditions have to be fulfilled with respect to the auxiliary acid to be used. Advantageously, according to the invention formic acid is employed as an auxiliary acid.

The reduction to the diol is likewise carried out under standard conditions (see, for example, WO 98/54188), where, for example, sodium borohydride is employed as a reductant, on use of which the indicated 7,8-transdiol can be obtained in over 90% diastereomeric purity. The etherification which follows if desired, which is likewise carried out in a manner habitual per se, leads to the compounds of the formula 1* in which R4a and R5b are hydrogen.

For the preparation of compounds of the formula 1 in which R5a and R5b are hydrogen, instead of compound 3, the starting materials to be used are 3-hydroxy-3-phenyl-propionic acid derivatives (appropriately protected on the hydroxyl group) in which Y (analogously to the above scheme) is a suitable leaving group.

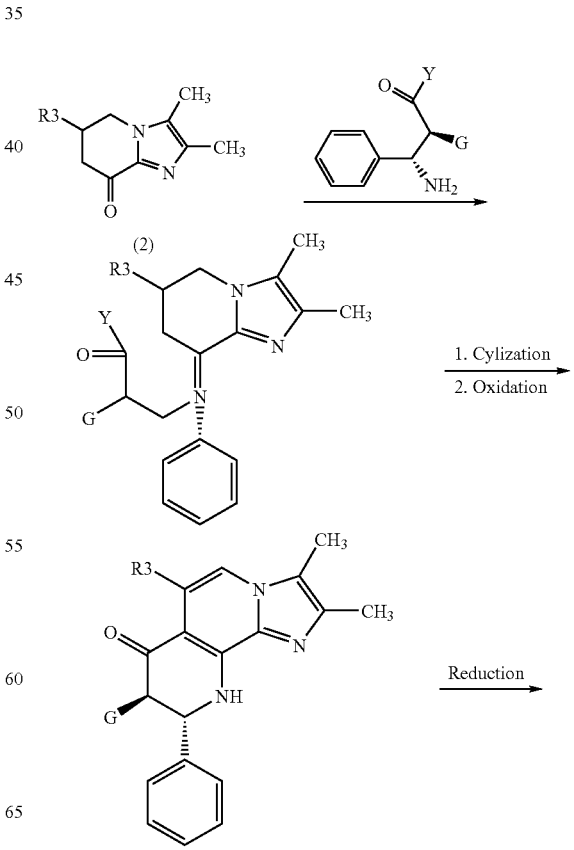

-continued

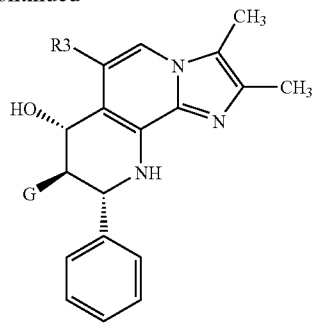

The above scheme 2 likewise, by way of example, is an enantioselective synthesis. Y is again a suitable leaving group, for example a methoxy group. The group G—depending on whether a compound where R5a and R5b=hydrogen or whether a compound R5a or R5b=hydroxyl is desired—is either hydrogen or a hydroxyl group (for example protected by a suitable silyl radical).

The reduction of the keto group with sodium borohydride following the cyclization leads—in the case in which G is a hydroxyl group—in over 90% diastereomeric purity to the 7,8-trans diol. The etherification following if desired, which is carried out according to known processes, leads to the final products of the formula 1* in which R4a and R5b are hydrogen. The corresponding 7,8-cis compound is obtained by chromatographic purification from the mother liquor which remains after the separation of the 7,8-trans compound.

The introduction of the "prodrug" radical R' subsequently to the synthesis carried out in accordance with scheme 1 or 2 is carried out in the sense of an acylation reaction starting from compounds of the formula 1 in which at least one of the radicals R4a, R4b, R5a and R5b is a hydroxyl group, by reaction with compounds of the formula R'-Z, in which Z is a suitable leaving group, for example a halogen atom. The reaction is carried out in a manner known per se, e.g. as described in the examples, preferably in the presence of a suitable auxiliary base. For the preparation of the compounds of the formula 1 in which R4a or R4b is 1–4C-alkoxy or 1–4C-alkoxy-1–4C-alkoxy and R5a or R5b is the radical R5', compounds of the formula 1 in which R4a or R4b is 1–4C-alkoxy or 1–4C-alkoxy-1–4C-alkoxy and R5a or R5b is hydroxyl are reacted with compounds R'-Z. For the preparation of the compounds of the formula 1 in which R4a or R4b is hydroxyl and R5a or R5b is the radical R5', compounds of the formula 1 in which R4a and R4b together are O (oxygen) and R5a or R5b is hydroxyl are reacted with compounds R'-Z. The reduction of the keto group to the hydroxyl group is then carried out. In a similar manner, compounds of the formula 1 are obtained in which the "prodrug" radical is in the 7-position and the hydroxyl or the 1–4C-alkoxy or 1–4C-alkoxy-1–4C-alkoxy radical is in the 8-position.

The isolation and purification of the substances according to the invention are carried out in a manner known per se, for example by distilling off the solvent in vacuo and recrystallizing the residue obtained from a suitable solvent or subjecting it to one of the customary purification methods, such as column chromatography on suitable support material.

Salts are obtained by dissolving the free compound in a suitable solvent, e.g. in a chlorinated hydrocarbon, such as methylene chloride or chloroform, or a low-molecular weight aliphatic alcohol (ethanol, isopropanol) which contains the desired acid, or to which the desired acid is then added. The salts are obtained by filtering, reprecipitating, precipitating with anonsolvent for the addition salt or by evaporating the solvent. Salts obtained can be converted by alkalization or by acidification into the free compounds, from which salts can in turn be prepared. In this manner, pharmacologically nontolerable salts can be converted into pharmacologically tolerable salts.

The pure enantiomers, in particular the pure enantiomers of the formula 1*, which are a preferred subject of the invention, can be obtained in a manner familiar to the person skilled in the art, for example by enantioselective synthesis (see, for example, the scheme), by chromatographic separation on chiral separating columns, by derivatization with chiral auxiliary reagents, subsequent diastereomer separation and removal of the chiral auxiliary group, by salt formation with chiral acids, subsequent resolution of the salts and release of the desired compound from the salt, or by (fractional) crystallization from a suitable solvent. Trans products obtained (e.g. compounds 1* where R4a and R5b=hydrogen) can be converted—at least partly—into the corresponding cis products (e.g. where R4b and R5b=hydrogen) by allowing to stand under acidic conditions (e.g. in 2 equivalents of acid, such as sulfuric acid) in the corresponding alcohol R4a-OH. Likewise, cis products can be converted into the correspondingtrans products. The cis and trans products are separated, for example, by chromatography or by crystallization.

The starting compounds of the formula 2 can be prepared starting from compounds known from the literature or with analogous use of processes known from the literature (e.g. Kaminski et al., J. Med. Chem. 1985, 28, 876–892), for example according to the general scheme 3 below:

Scheme 3
The scheme below outlines by way of example the preparation of a starting compound 2 where R3 = —COOC$_2$H$_5$.

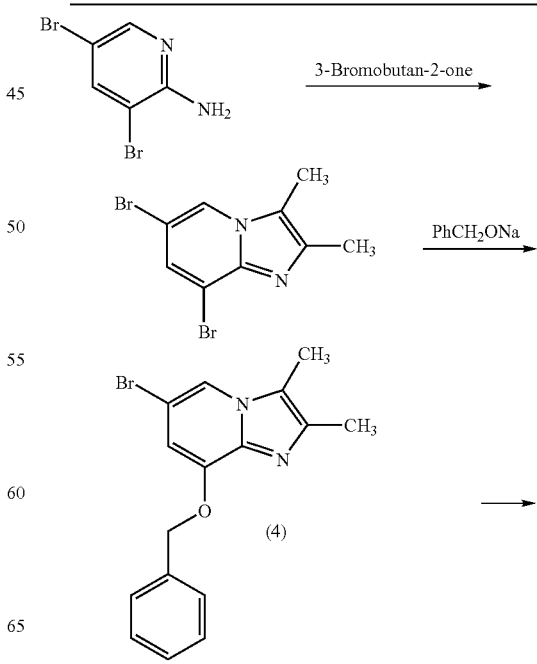

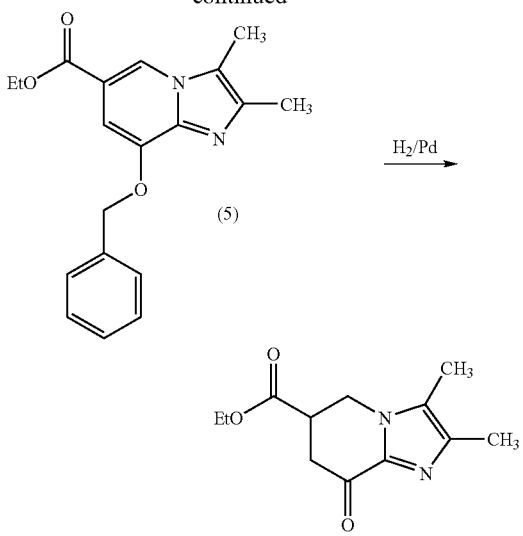

The reaction to give the compound 4 is carried out in a manner such as is known to the person skilled in the art. The reaction of 4 to 5 can be carried out in various ways, for example using the Heck reaction (with Pd(II), carbon monoxide and ethanol) or by metallation in the 6-position (with lithium or magnesium) and subsequent Grignard reaction. The metallation also offers the possibility of introducing other desired groups R3 in position 6, for example fluorine, chlorine or the carboxyl group. The debenzylation/reduction of the compound 5 is likewise carried out in a manner known per se, for example using hydrogen/Pd(0). If compounds where R3=—CO—NR5R6 are desired, an appropriate derivatization can be carried out in a manner known per se (conversion of an ester into an amide) at the stage of the compound 5 or after the debenzylation/reduction.

The following examples serve to illustrate the invention further without restricting it. Likewise, further compounds of the formula 1 whose preparation is not described explicitly can be prepared in an analogous manner or in a manner familiar per se to the person skilled in the art using customary process techniques. The abbreviation min stands for minute(s), h for hour(s) and ee for enantiomeric excess.

EXAMPLES

Final Products 1. (7S,8R,9R)-8-Acetoxy-7-(2-methoxyethoxy)-2,3-dimethyl-9-phenyl-7,8,9,10-tetra-hydroimidazo[1,2-h][1,7]naphthyridine A mixture of 1 g of (7S,8R,9R)-8-hydroxy-7-(2-methoxyethoxy)-2,3-dimethyl-9-phenyl-7,8,9,10-tetrahydroimidazo[1,2-h][1,7]naphthyridine, 0.1 g of sodium acetate (anhydrous) and 12 ml of acetic anhydride is stirred vigorously at room temperature for 4 h, then poured onto ice water, neutralized with 2 molar aqueous sodium hydroxide solution and extracted three times with 50 ml of ethyl acetate each time, the collected organic extracts are dried over potassium carbonate, the solvent is stripped off in vacuo and the residue is well dried in a high vacuum. 0.9 g of the title compound is obtained.

$^1$H-NMR (200 MHz, CDCl$_3$): δ=1.9 (s, 3H), 2.26 (s, 3H), 2.35 (s, 3H), 3.21 (s, 3H), 3.48 (d, 2H), 3.65 (m, 2H), 4.35 (d, 1H), 4.72 (dd, 1H), 5.3 (dd, 1H), 6.5 (d, 1H), 6.76 (d, 1H), 7.33 (s, 5H), 7.45 (d, 1H).

2. (7R,8R,9R)-8-Acetoxy-7-(2-methoxyethoxy)-2,3-dimethyl-9-phenyl-7,8,9,10-tetra-hydroimidazo[1,2-h][1,7]naphthyridine The title compound of melting point 129–31° C. (diethyl ether) is obtained analogously to example 1 by reaction of (7R,8R,9R)-8-hydroxy-7-(2-methoxyethoxy)-2,3-dimethyl-9-phenyl-7,8,9,10-tetrahydroimidazo[1,2-h][1,7]naphthyridine with acetic anhydride.

3. (7R,8R,9R)-8-Acetoxy-7-methoxy-2,3-dimethyl-9-phenyl-7,8,9,10-tetrahydro-imidazo[1,2-h][1,7]naphthyridine The title compound of melting point 197–99° C. (diethyl ether) is obtained analogously to example 1 by reaction of (7R,8R,9R)-8-hydroxy-7-methoxy-2,3-dimethyl-9-phenyl-7,8,9,10-tetrahydro-imidazo[1,2-h][1,7]naphthyridine with acetic anhydride.

4. (7R,8R,9R)8-Acetoxy-7-ethoxy-2,3-dimethyl-9-phenyl-7,8,9,10-tetrahydroimidazo-[1,2-h][1,7]naphthyridine The title compound of melting point 182–4° C. (diethyl ether) is obtained analogously to example 1 by reaction of (7R,8R,9R)-8-hydroxy-7-ethoxy-2,3-dimethyl-9-phenyl-7,8,9,10-tetrahydro-imidazo[1,2-h][1,7]naphthyridine with acetic anhydride.

5. (7R,8R,9R)-7-(2-Methoxyethoxy)-2,3-dimethyl-9-phenyl-8-propionyloxy-7,8,9,10-tetrahydroimidazo[1,2-h][1,7]naphthyridine A mixture of 2 g of (7R,8R,9R)-8-hydroxy-7-(2-methoxyethoxy)-2,3-dimethyl-9-phenyl-7,8,9,10-tetrahydroimidazo[1,2-h][1,7]naphthyridine and 24 ml of propionic anhydride is heated at 60° C. for 6 h, poured onto ice water after cooling, adjusted to pH 7.5 using dilute aqueous sodium hydroxide solution and extracted three times with 50 ml of ethyl acetate each time, the collected organic phases are dried over potassium carbonate and the volatile components are stripped off in vacuo. The oily residue which remains is intensively dried in a high vacuum and then triturated with a little cyclohexane. 1.2 g of the title compound are obtained as colorless crystals of melting point 106–7° C. (cyclohexane).

6. (7R,8R,9R)-8-Benzoyloxy-7-(2-methoxyethoxy)-2,3-dimethyl-9-phenyl-7,8,9,10-tetra-hydroimidazb[1,2-h][1,7]naphthyridine A mixture of 5 g of (7R,8R,9R)-8-hydroxy-7-(2-methoxyethoxy)-2,3-dimethyl-9-phenyl-7,8,9,10-tetrahydroimidazo[1,2-h][1,7]naphthyridine, 2.1 g of benzoyl chloride and 1.5 g of triethylamine in 60 ml of dry tetrahydrofuran is heated at 60° C. for 4 h, poured onto ice water after cooling and extracted three times with 50 ml of ethyl acetate each time, the collected organic phases are washed with a little water and dried over potassium carbonate, and the solvent is stripped off in vacuo. The oily residue which remains is purified on silica gel (eluent: diethyl ether). 2.5 g of the title compound are obtained as a colorless foam.

$^1$H-NMR (200 MHz, CDCl$_3$): δ=2.3 (s, 3H), 2.4 (s, 3H), 3.1 (s, 3H), 3.12 (dd, 3H), 3.4–3.58 (m, 3H), 4.71 (d, 1H), 4.92 (dd. 1H), 5.7 (dd, 1H), 6.55 (d, 1H), 6.72 (d, 1H), 7.22 (m, 3H), 7.40–7.50 (m, 5H), 7.6 (d, 1H), 7.82 (d, 2H).

7. (7S,8R,9R)-8-Benzoyloxy-7-(2-methoxyethoxy)-2,3-dimethyl-9-phenyl-7,8,9,10tetrahydroimidazo[1,2-h][1,7]naphthyridine Analogously to example 6, 1.1 g of the title compound of melting point 78–80° C. (diethyl ether) are obtained by reaction of (7S,8R,9R)-8-hydroxy-7-(2-methoxyethoxy)-2,3-dimethyl-9-phenyl-7,8,9,10-tetrahydroimidazo[1,2-h][1,7]naphthyridine with benzoyl chloride.

$^1$H-NMR (200 MHz, CDCl$_3$): δ=2.3 (s, 3H), 2.38 (s, 3H), 3.12 (s, 3H), 3.40–3.45 (m, 2H), 3.58–3.8 (m, 2H), 4.55 (d, 1H), 4.89–4.92 (dd, 1H), 5.50–5.55 (dd, 1H), 6.5 (d, 1H), 6.79–6.80 (d, 1H), 7.18–7.50 (m, 5H), 5.58–5.62 (m, 1H), 7.78–7.80 (d, 2H).

8. (7R,8R,9R)-8-Methoxycarbonyloxy-7-(2-methoxyethoxy)-2,3-dimethyl-9-phenyl-7,8,9,10-tetrahydroimidazo[1,2-h][1,7]naphthyridine A suspension of 2 g of (7R,8R,9R)-8-hydroxy-7-(2-methoxyethoxy)-2,3-dimethyl-9-phenyl-7,8,9,10-tetrahydroimidazo[1,2-h][1,7]naphthyridine in 30 ml of dry tetrahydrofuran is treated in small portions with 0.34 g of sodium hydride suspension (80% strength in paraffin) and stirred at room temperature for 30 minutes, then 0.66 g of methylchloroformate is added dropwise and the mixture is stirred for 3 h. It is then poured onto ice water, neutralized with semiconcentrated aqueous hydrochloric acid and extracted three times with a little ethyl acetate, and the collected organic phases are washed with a little water and dried over potassium carbonate. The volatile components are stripped off in vacuo and the solid residue is purified on silica gel (eluent: diethyl ether). 1.2 g of the title compound of melting point 176–77° C. (diethyl ether) are obtained.

9. (7S,8R,9R)-8-Methoxycarbonyloxy-7-(2-methoxyethoxy)-2,3-dimethyl-9-phenyl-7,8,9,10-tetrahydroimidazo[1,2-h][1,7]naphthyridine The title compound is obtained by reaction of (7S,8R,9R)-8-hydroxy-7-(2-methoxyethoxy)-2,3-dimethyl-9-phenyl-7,8,9,10-tetrahydroimidazo[1,2-h][1,7]naphthyridine with methyl chloroformate analogously to example 8.

$^1$H-NMR (200 MHz, CDCl$_3$): δ=2.28 (s, 3H), 2.32 (s, 3H), 3.2 (s, 3H), 3.41 (mp, 2H), 3.65 (mp, 2H), 4.38 (d, 1H), 4.75–4.80 (dd, 1H), 5.19–5.22 (dd, 1H), 6.59 (d, 1H), 6.71–6.78 (dd, 1H), 7.23–7.39 (mp, 5H), 7.42–7.50 (d, 1H).

10. (7R,8R,9R)-8-Benzoyloxy-7-methoxy-2,3-dimethyl-9-phenyl-7,8,9,10-tetrahydro-imidazo[1,2-h][1,7]naphthyridine The title compound of melting point 82–4° C. (ethyl acetate) is obtained by reaction of (7R,8R,9R)-8-hydroxy-7-methoxy-2,3-dimethyl-9-phenyl-7,8,9,10-tetrahydroimidazo[1,2-h][1,7]naphthyridine with benzoyl chloride analogously to example 6.

11. (7S,8R,9R)-8-Benzoyloxy-7-methoxy-2,3-dimethyl-9-phenyl-7,8,9,10-tetrahydro-imidazo[1,2-h][1,7]naphthyridine The title compound of melting point 78–80° C. (ethyl acetate) is obtained analogously to example 6 by reaction of (7S,8R,9R)-8-hydroxy-7-methoxy-2,3-dimethyl-9-phenyl-7,8,9,10-tetrahydro-imidazo [1,2-h][1,7]naphthyridine with benzoyl chloride.

12. (7R,8R,9R)-7-(2-Methoxyethoxy)-2,3-dimethyl-8-(4-nitrobenzoyloxy)-9-phenyl-7,8,9,10-tetrahydroimidazo[1,2-h][1,7]naphthyridine The title compound of melting point 133–4° C. (diethyl ether) is obtained analogously to example 8 by reaction of (7R,8R,9R)-8-hydroxy-7-(2-methoxyethoxy)-2,3-dimethyl-9-phenyl-7,8,9,10-tetra-hydroimidazo[1,2-h][1,7]naphthyridine with p-nitrobenzoyl chloride.

13. (7S,8R,9R)-7-(2-Methoxyethoxy)-2,3-dimethyl-8-(4-nitrobenzoyloxy)-9-phenyl-7,8,9,10-tetrahydroimidazo[1,2-h][1,7]naphthyridine The title compound is obtained as a colorless foam by reaction of (7S,8R,9R)-8-hydroxy-7-(2-methoxyethoxy)-2,3-dimethyl-9-phenyl-7,8,9,10-tetrahydroimidazo[1,2-h][1,7]naphthyridine with p-nitrobenzoyl chloride analogously to example 6.

$^1$H-NMR (200 MHz, CDCl$_3$): δ=2.29 (s, 3H), 2.38 (s, 3H), 3.11 (s, 3H), 3.38–3.42 (m, 2H), 3.61–3.78 (m, 2H), 4.52 (d, 1H), 4.9–4.92 (dd, 1H), 5.58–5.6 (dd, 1H), 6.59 (d, 1H), 6.79–6.82 (d, 1H), 7.22–7.48 (m, 5H), 7.45–7.50 (d, 1H), 8.00–8.05 (d, 2H), 8.30–8.35 (d, 2H).

14. (7S,8R,9R)-7-(2-Methoxyethoxy)-2,3-dimethyl-8-(3-nitrobenzoyloxy)-9-phenyl-7,8,9,10-tetrahydroimidazo[1,2-h][1,7]naphthyridine The title compound is obtained as a colorless viscous oil by reaction of (7S,8R,9R)-8-hydroxy-7-(2-methoxyethoxy)-2,3-dimethyl-9-phenyl-7,8,9,10-tetrahydroimidazo[1,2-h][1,7]naphthyridine with 3-nitrobenzoyl chloride analogously to example 6.

$^1$H-NMR (200 MHz, CDCl$_3$): δ=2.3 (s, 3H), 2.39 (s, 3H), 3.15 (s, 3H), 3.39–3.47 (m, 2H), 3.61–3.80 (m, 2H), 4.55–4.59 (d, 1H), 4.91–4.99 (dd, 1H), 5.55–5.61 (dd, 1H), 6.57–6.58 (d, 1H), 6.80–6.82 (d, 1H), 7.25–7.52 (m, 5H), 7.69–7.88 (m, 1H), 8.15–8.31 (d, 1H), 8.42–8.50 (m, 2H).

15. (7R,8R9R)-7ethyl-8-(3-nitrobenzoyloxy)-9-phenyl-7,8,9,10-tetrahydroimidazo[1,2-h][1,7]naphthyridine The title compound of melting point 73–75° C. (diethyl ether) is obtained by reaction of (7R,8R,9R)-8-hydroxy-7-(2-methoxyethoxy)-2,3-dimethyl-9-phenyl-7,8,9,10-tetrahydroimidazo[1,2-h][1,7]naphthyridine with 3-nitrobenzoyl chloride analogously to example 6.

16. (7S,8R,9R)-7-Methoxy-2,3-dimethyl-8-(3-nitrobenzoyoxy)-9-phenyl-7,8,9,10-tetra-hydroimidazo[1,2-h][1,7]naphthyridine The title compound of melting point 120–22° C. (acetone) is obtained by reaction of (7S,8R,9R)-8-hydroxy-7-methoxy-2,3-dimethyl-9-phenyl-7,8,9,10-tetrahydroimidazo[1,2-h][1,7]naphthyridine with 3-nitrobenzoyl chloride analogously to example 6.

17. (7R,8R,9R)-7-Methoxy-2,3-dimethyl-8-(3-nitrobenzoyloxy)-9-phenyl-7,8,9,10-tetra-hydroimidazo[1,2-h][1,7]naphthyridine The title compound of melting point 80–84° C. (diethyl ether) is obtained by reaction of (7R,8R,9R)-8-hydroxy-7-methoxy-2,3-dimethyl-9-phenyl-7,8,9,10-tetrahydroimidazo[1,2-h][1,7]naphthyridine with 3-nitrobenzoyl chloride analogously to example 6.

18. (7S,8R,9R)-7-(2-Methoxyethoxy)-2,3-dimethyl-8-(4-methoxybenzoyloxy)-9-phenyl-7,8,9,10-tetrahydroimidazo[1,2-h][1,7]naphthyridine The title compound of melting point 82–83° C. (diethyl ether) is obtained analogously to example 6 by reaction of (7S,8R,9R)-8-hydroxy-7-(2-methoxyethoxy)-2,3-dimethyl-9-phenyl-7,8,9,10-tetra-hydroimidazo[1,2-h][1,7]naphthyridine with 4-methoxybenzoyl chloride.

19. (7R,8R,9R)-7-(2-Methoxyethoxy)-2,3-dimethyl-8-(4-methoxybenzoyloxy)-9-phenyl-7,8,9,10-tetrahydroimidazo[1,2-h][1,7]naphthyridine The title compound of melting point 150–51° C. (diethyl ether) is obtained analogously to example 6 by reaction of (7R,8R9R)-8-hydroxy-7-(2-methoxyethoxy)-2,3-dimethyl-9-phenyl-7,8,9,10-tetrahydroimidazo[1,2-h][1,7]naphthyridine with 4-methoxybenzoyl chloride.

20. (7R,8R,9R)-7-(2-Methoxyethoxy)-2,3-dimethyl-8-(N,N-dimethylaminomethyl-carbonyloxy)-9-phenyl-7,8,9,10-tetrahydroimidazo[1,2-h][1,7]naphthyridine The title compound of melting point 114–5° C. (diethyl ether) is obtained analogously to example 8 by reaction of (7R,8R,9R)-8-hydroxy-7-(2-methoxyethoxy)-2,3-dimethyl-9-phenyl-7,8,9,10-tetra-hydroimidazo[1,2-h][1,7]naphthyridine with N,N-dimethylglycine chloride hydrochloride prepared in situ.

21. (7S,8R,9R)-7-(2-Methoxyethoxy)-2,3-dimethyl-8-(N,N-dimethylaminomethyl-carbonyloxy)-9-phenyl-7,8,9,10-tetrahydroimidazo[1,2-h][1,7]naphthyridine The title compound of melting point 206–7° C. (diethyl ether) is obtained analogously to example 8 by reaction of (7S,8R,9R)-8-hydroxy-7-(2-methoxyethoxy)-2,3-dimethyl-9-phenyl-7,8,9,10-tetrahydroimidazo[1,2-h][1,7]naphthyridine with N,N-dimethylglycine chloride hydrochloride prepared in situ.

22. (7S,8R,9R)-7-(2-Methoxyethoxy)-8-(N,N-diethylaminocarbonyloxy)-2,3-dimethyl-9-phenyl-7,8,9,10-tetrahydroimidazo[1,2-h][1,7]naphthyridine The title compound of melting point 50–52° C. is obtained analogously to example 8 by reaction of (7S,8R,9R)-8-hydroxy-7-(2-methoxyethoxy)-2,3-dimethyl-9-phenyl-7,8,9,10-tetrahydro-imidazo[1,2-h][1,7]naphthyridine with N,N-diethylcarbamoyl chloride.

23. (7R,8R,9R)-7-(2-Methoxyethoxy)-8-(N,N-diethylaminocarbonyloxy)-2,3-dimethyl-9-phenyl-7,8,9,10-tetrahydroimidazo[1,2-h][1,7]naphthyridine The title compound is obtained as a yellowish foam by reaction of (7R,8R,9R)-8-hydroxy-7-(2-methoxyethoxy)-2,3-dimethyl-9-phenyl-7,8,9,10-tetrahydroimidazo[1,2-h][1,7]naphthyridine with N,N-diethylcarbamoyl chloride analogously to example 8.

$^1$H-NMR (200 MHz, CDCl$_3$): δ=0.9 (m, 6H), 2.3 (s, 3H), 2.4 (s, 3H), 3.08 (m, 4H), 3.1 (s, 3H), 3.12 (m, 2H), 3.29–3.50 (m, 2H), 4.5 (d, 1H), 4.76 (dd, 1H), 5.38 (dd, 1H), 6.43 (d, 1H), 6.7 (d, 1H), 7.3 (m, 5H), 7.46 (d, 1H).

24. (7R,8R9R)-8-Ethylaminocarbonyloxy-7-(2-methoxyethoxy)-2,3dimethyl-9-phenyl-7,8,9,10-tetrahydroimidazo[1,2-h][1,7]naphthyridine The title compound is obtained as a yellowish solid after reaction of (7R,8R,9R)-8-hydroxy-7-(2-methoxyethoxy)-2,3-dimethyl-9-phenyl-7,8,9,10-tetrahydroimidazo[1,2-h][1,7]naphthyridine with ethyl isocyanate analogously to example 5.

$^1$H-NMR (200 MHz, CDCl$_3$): δ=0.91–1.0 (m, 3H), 2.29 (s, 3H), 2.32 (s, 3H), 3.02 (s, 5H), 3.32–3.45 (m, 4H), 4.38 (d, 1H), 4.8 (s, 1H), 5.39 (m, 1H), 6.62–6.70 (d, 2H), 7.12–7.32 (m, 5H), 7.40–7.45 (d, 1H).

25. (7S,8R,9R)-8-Ethylaminocarbonyloxy-7-(2-methoxyethoxy)-2,3-dimethyl-9-phenyl-7,8,9,10-tetrahydroimidazo[1,2-h][1,7]naphthyridine The title compound is obtained as a pale brown solid after reaction of (7S,8R,9R)-8-hydroxy-7-(2-methoxyethoxy)-2,3-dimethyl-9-phenyl-7,8,9,10-tetrahydroimidazo[1,2-h][1,7]naphthyridine with ethyl isocyanate analogously to example 5.

$^1$H-NMR (200 MHz, CDCl$_3$): δ=0.90–0.99 (m, 5H), 2.29 (s, 3H), 2.35 (s, 3H), 2.9–3.0 (m, 2H), 3.21 (s, 3H), 3.39–3.50 (m, 4H), 4.31 (d, 1H), 4.69–4.76 (dd, 1H), 5.2–5.28 (dd, 1H), 6.4–6.45 (d, 1H), 6.75–7.90 (d, 1H), 7.09–7.14 (m, 1H), 7.26–7.4 (m, 5H), 7.41–7.45 (d, 1H).

26. (7R,8R,9R)-8-[(+)-Menthyloxycarbonyloxy]-7-(2-methoxyethoxy)-2,3-dimethyl-9-phenyl-7,8,9,10-tetrahydroimidazo[1,2-h][1,7]naphthyridine.

The title compound of melting point 127–9° C. (diethyl ether) is obtained by reaction of (7R,8R,9R)-8-hydroxy-7-(2-methoxyethoxy)-2,3-dimethyl-9-phenyl-7,8,9,10-tetrahydro-imidazo[1,2-h][1,7]naphthyridine with menthyl(+)-chloroformate analogously to example 6.

27. (7S,8R,9R)-8-[(+)-Menthyloxycarbonyloxy]-7-(2-methoxyethoxy)-2,3-dimethyl-9-phenyl-7,8,9,10-tetrahydroimidazo[1,2-h][1,7]naphthyridine The title compound of melting point 63–65° C. (diethyl ether) is obtained by reaction of (7S,8R,9R)-8-hydroxy-7-(2-methoxyethoxy)-2,3-dimethyl-9-phenyl-7,8,9,10-tetrahydro-imidazo[1,2-h][1,7]naphthyridine with menthyl(+)-chloroformate analogously to example 6.

28. (7R,8R,9R)-7-(2-Methoxyethoxy)-8-(0-methyl-succinoyloxy)-2,3-dimethyl-9-phenyl-7,8,9,10-tetrahydroimidazo[1,2-h][1,7]naphthyridine The title compound of melting point 73–4° C. (diisopropyl ether) is obtained by reaction of (7R,8R,9R)-8-hydroxy-7-(2-methoxyethoxy)-2,3-dimethyl-9-phenyl-7,8,9,10-tetrahydro-imidazo[1,2-h][1,7]naphthyridine with monomethyl succinyl chloride analogously to example 8.

29. (7S,8R,9R)-7-(2-Methoxyethoxy)-8(0-methyl-succinoyloxy)2,3-dimethyl-9-phenyl-7,8,9,10-tetrahydroimidazo[1,2-h][1,7]naphthyridine The title compound of melting point 50–1° C. (diethyl ether) is obtained by reaction of (7S,8R,9R)-8-hydroxy-7-(2-methoxyethoxy)-2,3-dimethyl-9-phenyl-7,8,9,10-tetrahydroimidazo[1,2-h][1,7]-naphthyridine with monomethyl succinyl chloride analogously to example 8.

30. (7R,8R,9R)-7-(2-Methoxyethoxy)-8-(0-methyl-malonyloxy)-2,3-dimethyl-9-phenyl-7,8,9,10-tetrahydroimidazo[1,2-h][1,7]naphthyridine The title compound of melting point 70–1° C. (diethyl ether/diisopropyl ether) is obtained by reaction of (7R,8R,9R)-8-hydroxy-7-(2-methoxyethoxy)-2,3-dimethyl-9-phenyl-7,8,9,10-tetra-hydroimidazo[1,2-h][1,7]naphthyridine with monomethyl malonyl chloride analogously to example 8.

31. (7S,8R,9R)-7-(2Methoxyethoxy)-8-(0-methyl-malonyloxy)-2,3-dimethyl-9-phenyl-7,8,9,10-tetrahydroimidazo[1,2-h][1,7]naphthyridine The title compound is obtained as an amorphous solid after reaction of (7S,8R,9R)-8-hydroxy-7-(2-methoxyethoxy)-2,3-dimethyl-9-phenyl-7,8,9,10-tetrahydroimidazo[1,2-h][1,7]naphthyridine with monomethyl malonyl chloride analogously to example 8.
$^1$H-NMR (200 MHz, CDCl$_3$): δ=2.1 (s, 3H), 2.35 (s, 3H), 3.21 (s, 3H), 3.39 (s, 2H), 3.46 (s, 2H), 3.57 (s, 3H), 3.60–3.71 (m, 2H), 4.39 (d, 1H), 4.70–4.78 (dd, 1H), 5.31–5.39 (dd, 1H), 6.48 (d, 1H), 6.77–6.79 (d, 1H), 7.31 (s, 5H), 7.45–7.50 (d, 1H).

32. (7R,8R,9R)-7-(2-Methoxyethoxy)-8-(0-ethyloxaloyloxy)-2,3-dimethyl-9-phenyl-7,8,9,10-tetrahydroimidazo[1,2-h][1,7]naphthyridine The title compound is obtained as an amorphous solid after reaction of (7R,8R,9R)-8-hydroxy-7-(2-methoxyethoxy)-2,3-dimethyl-9-phenyl-7,8,9,10-tetrahydroimidazo[1,2-h][1,7]naphthyridine with monoethyl oxalyl chloride analogously to example 8.
$^1$H-NMR (200 MHz, CDCl$_3$): δ=1.19–1.22 (m, 3H), 2.3 (s, 3H), 2.36 (s, 3H), 3.09 (s, 5H), 3.19 (s, 2H), 3.51–3.64 (m, 2H), 4.19–4.29 (dd, 2H), 4.61 (d, 1H), 4.81–4.90 (m, 1H), 5.50–5.57 (m, 1H), 6.6 (d, 1H), 6.69–6.71 (d, 1H), 7.21–7.39 (m, 5H), 7.50–7.52 (d, 1H).

33. (7S,8R,9R)-8-(0-Ethyloxaloyloxy)-7-(2-methoxyethoxy)-2,3-dimethyl-9-phenyl-7,8,9,10-tetrahydroimidazo[1,2-h][1,7]naphthyridine The title compound is obtained as an yellowish solid after reaction of (7S,8R,9R)-8-hydroxy-7-(2-methoxyethoxy)-2,3-dimethyl-9-phenyl-7,8,9,10-tetrahydroimidazo[1,2-h][1,7]naphthyridine with monoethyl oxalyl chloride analogously to example 8.
$^1$H-NMR (200 MHz, CDCl$_3$): δ=1.20–1.28 (m, 3H), 2.3 (s, 3H), 2.38 (s, 3H), 3.2 (s, 3H), 3.41–3.49 (m, 2H), 3.60–3.71 (m, 2H), 4.19–4.29 (dd, 2H), 4.42–4.48 (s, 1H), 4.80–4.88 (dd, 1H), 5.48–5.51 (dd, 1H), 6.6 (d, 1H), 6.78–6.80 (d, 1H), 7.35 (s, 5H), 7.49–7.51 (d, 1H).

34. (7R,8R,9R)-8-Formyloxy-(2-methoxyethoxy)-2,3-dimethyl-9-phenyl-7,8,9,10-tetra-hydroimidazo[1,2-h][1,7]naphthyridine The title compound of melting point 156–7° C. (tetrahydrofuran/diethyl ether) is obtained by reaction of (7R,8R,9R)-8-hydroxy-7-(2-methoxyethoxy)-2,3-dimethyl-9-phenyl-7,8,9,10-tetra-hydroimidazo[1,2-h][1,7]naphthyridine with phenyl formate analogously to example 5.

35. (7S,8R,9R)-8-Formyloxy-(2-methoxyethoxy)-2,3-dimethyl-9-phenyl-7,8,9,10-tetra-hydroimidazo[1,2-h][1,7]naphthyridine The title compound is obtained as a greenish-yellow solid after reaction of (7S,8R,9R)-8-hydroxy-7-(2-methoxyethoxy)-2,3-dimethyl-9-phenyl-7,8,9,10-tetrahydroimidazo[1,2-h][1,7]-naphthyridine with phenyl formate analogously to example 5.

36. (7R,8R,9R)-8-Benzoyloxy-2,3-dimethyl-7-(2-methoxyethoxy)-9-phenyl-7H-8,9-dihydropyrano[2,3-c]imidazo[1,2-a]pyridine To a solution of 0.50 g (1.36 mmol) (7R,8R,9R)-2,3-dimethyl-8-hydroxy-7-(2-methoxyethoxy)-9-phenyl-7H-8,9-dihydropyrano[2,3-c]imidazo[1,2-a]pyridine, 1.0 ml (6.80 mmol) triethylamine and 1.60 mg (0.01 mmol) DMAP in dichloromethane (5.0 ml) is added at 0° C. 0.48 ml (4.08 mmol) benzoyl chloride. The mixture is warmed up to 25° C. and stirred for 2 h at this temperature. Subsequently the mixture is quenched by adding saturated aqueous sodium hydrogen carbonate solution. After separation of the organic layer the water layer is extracted with dichloromethane twice. The combined organic layers are washed with brine, dried over sodium sulphate and evaporated in vacuo. The crude product is purified by column chromatography (diethyl ether/triethylamine: 9/1) to give 0.59 g (1.25 mmol/ 91%) of the title compound as a colourless solid of melting point 130–133° C. (diethyl ether).

37. (7S,8R,9R)-8-Benzoyloxy-2,3-dimethyl-7-(2-methoxyethoxy)-9-phenyl-7H-8,9-dihydropyrano[2,3-c]imidazo[1,2-a]pyridine The title compound of melting point 135–6° C. (diethyl ether) is obtained as described in example 36 by reaction of (7S,8R,9R)-2,3-dimethyl-8-hydroxy-7-(2-methoxyethoxy)-9-phenyl-7H-8,9-dihydropyrano[2,3-c]imidazo[1,2-a]pyridine with benzoyl chloride.

38. (7R,8R,9R)-8-[4-(Methoxycarbonyl)-benzoyloxy]-2,3-dimethyl-7-(2-methoxyethoxy)-9-phenyl-7H-8,9-dihydropyrano[2,3-c]imidazo[1,2-a]pyridine To a solution of 0.50 g (1.36 mmol) (7R,8R,9R)-2,3-dimethyl-8-hydroxy-7-(2-methoxyethoxy)-9-phenyl-7H-8,9-dihydro-pyrano[2,3-c]imidazo[1,2-a]pyridine, 1.0 ml (6.80 mmol) triethylamine and 1.60 mg (0.01 mmol) DMAP in dichloromethane (5.0 ml) is added at 0° C. 0.83 g (4.08 mmol) terephthaloyl chloride. The mixture is warmed up to 25° C. and stirred for 2 h at this temperature following by adding of methanol (5.0 ml) and stirring for further 2 h. Subsequently the mixture is quenched by adding saturated aqueous sodium hydrogen carbonate solution. After separation of the organic layer the water layer is extracted with dichloromethane twice. The combined organic layers are washed with brine, dried over sodium sulphate and evaporated in vacuo. The crude product is purified by column chromatography (diethyl ether/triethylamine: 9/1) to give 0.21 g (0.40 mmol/29%) of the title compound as a colourless solid of melting point 156–160° C. (diethyl ether).

39. (7S,8R,9R)-8-[4-(Methoxycarbonyl)-benzoyloxy]-2,3-dimethyl-7-(2-methoxyethoxy). 9-phenyl-7H-8,9-dihydropyrano[2,3-c]imidazo[1,2-a]pyridine The title compound of melting point 71° C. (sintering) is obtained analogously to example 38 by reaction of (7S,8R,9R)-2,3-dimethyl-8-hydroxy-7-(2-methoxyethoxy)-9-phenyl-7H-8,9-dihydro-pyrano[2,3-c]imidazo[1,2-a]pyridine with monomethyl terephthaloyl chloride.

40. (7S,8R,9R)-2,3-Dimethyl-7-methoxy-8-methoxyacetyloxy-9-phenyl-7,8,9,10-tetrahydroimidazo[1,2-h][1,7]naphthyridine The title compound of m.p. 73–75° C. is obtained analogously to example 6 after purification on silica gel.

41. (7R,8R,9R)8-(N,N-Diethylaminocarbonyloxy)-2,3-dimethyl-7-methoxy-9-phenyl 7,8,9,10-tetrahydroimidazo[1,2-h][1,7]naphthyridine The title compound of m.p. 123–124° C. is obtained analogously to example 6 after purification on silica gel.

42. (7S,8R,9R)8-(N,N-Diethylaminocarbonyloxy)-2,3-dimethyl-7-methoxy-9-phenyl 7,8,9,10-tetrahydroimidazo[1,2-h][1,7]naphthyridine The title compound of m.p. 97–98° C. is obtained analogously to example 6 after purification on silica gel.

43. (7R,8R,9R)7-Methoxy-8-methoxycarbonyloxy-2,3-dimethyl-9-phenyl 7,8,9,10-tetrahydroimidazo[1,2-h][1,7]naphthyridine The title compound of m.p. 178–179° C. is obtained analogously to example 6 after purification on silica gel.

44. (7S,8R,9R)7-Methoxy-8-methoxycarbonyloxy-2,3-dimethyl-9-phenyl 7,8,9,10-tetrahydroimidazo[1,2-h][1,7]naphthyridine The title compound of m.p. 90–91° C. is obtained analogously to example 6 after purification on silica gel.

45. (7R,8R,9R)-2,3-Dimethyl-8-formyloxy-7-methoxy-9-phenyl-7,8,9,10-tetrahydro-imidazo[1,2-h][1,7]naphthyridine The title compound of m.p. 152–153° C. is obtained analogously to example 6 after purification on silica gel.

46. (7S,8R,9R)-2,3-Dimethyl-8-formyloxy-7-methoxy-9-phenyl-7,8,9,10-tetrahydro-imidazo[1,2-h][1,7]naphthyridine The title compound is obtained as a yellowish solid analogously to example 6 after purification on silica gel.

47. (7R,8R,9R)-8-Benzoyloxy-2,3-dimethyl-7-methoxy-9-phenyl-7,8,9,10-tetrahydro-imidazo[1,2-h][1,7]naphthyridine The title compound of m.p. 92–93° C. is obtained analogously to example 6 after purification on silica gel.

Starting Compounds

A. 6,8-Dibromo-2,3-dimethylimidazo[1,2-a]pyridine

A mixture of 31.8 g of 2-amino-3,5-dibromopyridine, 22 g of 3-bromo-2-butanone and 350 ml of tetrahydrofuran is heated to reflux for 9 days, and the precipitate formed is filtered off and dried in vacuo. It is then suspended in 1 l of water and adjusted to pH 8 using 6 molar aqueous sodium hydroxide solution. The precipitate formed here is filtered off and washed with water. 28 g of the title compound of melting point above 90° C. (sintering) are obtained.

B. 8-Benzyloxy-6-bromo-2,3-dimethylimidazo[1,2-a]pyridine 34.8 ml of benzyl alcohol are added dropwise with ice-cooling to a suspension of 13.5 g of sodium hydride (60% strength suspension in paraffin) in 510 ml of dimethylformamide and the mixture is stirred for 1 h until the evolution of gas is complete. 51.2 g of 6,8-dibromo-2,3-dimethylimidazo[1,2-a]pyridine are then introduced in small portions and the mixture is stirred at room temperature for 40 h. It is then poured onto 1 l of ice water and extracted three times with 100 ml of dichloromethane each time. The combined organic extracts are washed with saturated ammonium chloride solution and twice with water, and concentrated to dryness in vacuo and the residue is stirred with a little ethyl acetate. The precipitate obtained here is filtered off and dried in vacuo. 43.2 g of the title compound of melting point 151–3° C. (ethyl acetate) are obtained.

C. 8-Benzyloxy-6-ethoxycarbonyl-2,3-dimethylimidazo[1,2-a]pyridine

A mixture of 4 g of 8-benzyloxy-6-bromo-2,3-dimethylimidazo[1,2-a]pyridine, 0.4 g of palladium(II) acetate, 1.33 g of triphenylphosphine, 10 ml of triethylamine and 50 ml of ethanol is heated in a carbon monoxide atmosphere in an autoclave (5 bar) for 16 h, the volatile components are stripped off in vacuo and the residue is chromatographed on silica gel (eluent: ethyl acetate). 2.4 g of the title compound of melting point 140–1° C. (diethyl ether) are obtained.

D. 6-Ethoxycarbonyl-2,3-dimethyl-5,6,7,8-tetrahydroimidazo[1,2-a]pyridin-8-one 3 g of 8-benzyloxy-6-ethoxycarbonyl-2,3-dimethylimidazo[1,2-a]pyridine, suspended in 50 ml of ethanol, are treated with 0.5 g of 10% strength palladium/active carbon and hydrogenated under a hydrogen pressure of 50 bar for 20 hours at an oil bath temperature of 75° C. After cooling, the catalyst is filtered off, the filtrate is concentrated to ⅕ of the volume in vacuo and the colorless precipitate formed here is filtered off. The filtrate from the precipitate is concentrated to dryness and chromatographed on silica gel (eluent: methylene chloride/methanol 100/3). 0.32 g of 6-ethoxycarbonyl-8-hydroxy-2,3-dimethyl-5,6,7,8-tetrahydroimidazo[1,2-a]pyridine is obtained. For conversion into the title compound, it is dissolved in chloroform, treated with 1.6 g of manganese dioxide and the mixture is stirred at room temperature for 20 h. The solid is then filtered off, the filtrate is concentrated to dryness in vacuo and the residue obtained is purified on silica gel (eluent: methylene chloride/methanol 13/1). 0.2 g of the title compound of melting point 138–40° C. (diethyl ether) is obtained.

E. 8-Benzyloxy-6-hydroxymethyl-2,3-dimethylimidazo[1,2-a]pyridine

A solution of 1.2 g of 8-benzyloxy-6-ethoxycarbonyl-2, 3-dimethylimidazo[1,2-a]pyridine in 20 ml of tetrahydrofuran is treated in small portions with 0.2 g of lithium aluminium hydride at room temperature, stirred for 1 hour and successively treated with 0.2 ml of water, 0.2 ml of 6 molar sodium hydroxide solution and 0.6 ml of water. The mixture is then extracted twice with methylene chloride (50 ml each), the combined organic phases are concentrated to dryness in vacuo and the residue is purified on silica gel (eluent: methylene chloride/methanol 13/1). 0.4 g of the title compound of melting point 213–5° C. (acetone) is obtained.

F. 6-Hydroxymethyl-2,3-dimethyl-5,6,7,8-tetrahydroimidazo[1,2-a]pyridin-8-one Analogously to the process described in example D, the title compound is obtained starting from 8-benzyloxy-6-hydroxymethyl-2,3-dimethylimidazo[1,2-a]pyridine by debenzylation/hydrogenation using palladium/active carbon.

G. 2,3-Dimethyl-6,7-dihydro-5H-imidazo[1,2-a]pyridin-8-one a) 500 g (2.35 mol) of 8-amino-2,3-dimethylimidazo[1, 2-a]pyridine (see EP-A-299470) and 150 g of palladium on active carbon (10% Pd), suspended in 5.01 of 6N hydrochloric acid, are stirred at 50° C. for 24 h under a hydrogen pressure of 10 bar. The catalyst is filtered off and the reaction mixture is concentrated to 2.0 l in vacuo. The solution obtained is extracted with dichloromethane. The aqueous phase is adjusted to pH 4.8–5.0 using concentrated ammonia solution and again extracted with dichloromethane. This procedure is repeated ten times. The combined organic phases are dried over sodium sulfate and concentrated. The crude product is crystallized from isopropanol. 334.1 g of the title compound are obtained in the form of pale brown crystals of melting point 178.5° C. (isopropanol).

Alternatively, the title compound can be obtained as follows:
b) A mixture of 252 g of 8-benzyloxy-2,3-dimethylimidazo[1,2-a]pyridine, 84 g of sodium hydrogencarbonate, 27 g of palladium/carbon catalyst (10% strength) in 500 ml of methanol is initially hydrogenated with hydrogen (5 bar) in an autoclave at 40° C. (20 h). The temperature is then reduced to 20° C. and the hydrogen pressure to 2 bar and hydrogenation is continued until the completion of the slow absorption of hydrogen (about 10 h, TLC checking). The catalyst is then filtered off, the filter cake is washed with 200 ml of methanol, the filtrate is concentrated to dryness in vacuo, the residue is stirred with 200 ml of chloroform and insoluble material is filtered off. The filter cake is washed well with 150 ml of chloroform and the filtrate is concentrated to dryness in vacuo. 142 g of the title compound of melting point 178–9° C. (2-propanol) are obtained.

H. 2-Methyl-6,7-dihydro-5H-imidazo[1,2-a]pyridin-8-one

Analogously to the process described in example Ga, the title compound is obtained starting from the compound 8-amino-2-methylimidazo[1,2-a]pyridine described in EP-A-299470.

I. 3-Formyl-2-methyl-6,7-dihydro-5H-imidazo[1,2-a]pyridin-8-one

Analogously to the process described in example Ga, the title compound is obtained starting from the compound 8-amino-2-formyl 2-methylimidazo[1,2-a]pyridine described in EP-A-299470.

J. 6-Chlor-2-methyl-6,7-dihydro-5H-imidazo[1,2-a]pyridin-8-one

Analogously to the process described in example D, the title compound is obtained starting from 8-benzyloxy-6-chloro-2-methylimidazo[1,2-a]pyridine (EP-A-299470) by debenzylation/hydrogenation using palladium/active carbon.

K. 6-Chlor-3-formyl-2-methyl-6,7-dihydro-5H-imidazo[1,2-a]pyridin-8-one

Analogously to the process described in example D, the title compound is obtained starting from 8-benzyloxy-6-chloro-3-formyl-2-methylimidazo[1,2-a]pyridine (EP-A-299470) by debenzylation/hydrogenation using palladium/active carbon.

L. (7R,8R,9R)-2,3-Dimethyl-8-hydroxy-7-methoxy-9-phenyl-7,8,9,10-tetrahydroimidazo-[1,2-h][1,7]naphthyridine Method a
20 g (65 mmol) of (7R,8R,9R)-2,3-dimethyl-7,8-dihydroxy-9-phenyl-7,8,9,10-tetrahydroimidazo-[1,2-h][1,7]naphthyridine (WO 98/42707) are dissolved in 350 ml of methanol. 13.5 g of sulfuric acid are added and the solution is stirred at 50° C. for 48 h. After cooling, the reaction mixture is poured into 250 ml of water. The pH is brought to a neutral value by addition of saturated aqueous sodium hydrogencarbonate solution. The precipitate is collected and purified on silica gel (eluent: diethyl ether). 2.5 g of the title compound are obtained as colorless crystals of melting point 164–165° C. (2-propanol).

Method b
10 g (32.5 mmol) of (7R,8R,9R)-2,3-dimethyl-7,8-dihydroxy-9-phenyl-7,8,9,10-tetrahydro-imidazo[1,2-h][1,7]naphthyridine are dissolved in 200 ml of dry dimethylformamide. 1.9 g of commercially obtainable sodium hydride in paraffin (80%) are added in small portions at room temperature. After 1 h, 9.1 g (65 mmol) of methyl iodide dissolved in 4 ml of dimethylformamide are added and the mixture is stirred for a further hour. The reaction mixture is then poured into cold water. 20 ml of a saturated aqueous ammonium chloride solution are added, and the yellow precipitate is collected and discarded. The filtrate is extracted a number of times with ethyl acetate, the combined organic phases are washed a number of times with water and the solvent is evaporated in vacuo. The solid residue is purified on silica gel (diethyl ether). 2 g of the title compound are obtained as colorless crystals of melting point 164–165° C. (2-propanol).

M. (7S,8R,9R)-2,3-Dimethyl-8-hydroxy-7-methoxy-9-phenyl-7,8,9,10-tetrahydroimidazo-[1,2-h][1,7]naphthyridine 6 g of the title compound are obtained as a colorless powder of melting point 108–110° C. after purification on silica gel according to example L, method a, starting from (7S,8R,9R)-2,3-dimethyl-7,8-dihydroxy-9-phenyl-7,8,9,10-tetrahydroimidazo[1,2-h][1,7]naphthyridine.

N. (7R,8R,9R)-2,3-Dimethyl-7-ethoxy-8-hydroxy-9-phenyl-7,8,9,10-tetrahydroimidazo-[1,2-h][1,7]naphthyridine 500 mg of the title compound are obtained by reaction of (7R,8R,9R)-2,3-diemthyl-7,8-dihydroxy-9-phenyl-7,8,9,10-tetrahydroimidazo[1,2-h][1,7]naphthyridine with methanol and sulfuric acid according to example L, method a, after purification on silica gel (eluent: diethyl ether). Melting point: 188–190° C.

O. (7S,8R,9R)-2,3-Dimethyl-7-ethoxy-8-hydroxy-9-phenyl-7,8,9,10-tetrahydroimidazo-[1,2-h][1,7]naphthyridine 800 mg of the title compound of melting point 143–144° C. are obtained as a solid by further purification of the mother liquor from example N on silica gel.

P. (7R,8R,9R)-2,3-Dimethyl-8-hydroxy-7-(2-methoxyethoxy)-9-phenyl-7,8,9,10-tetrahydro-imidazo[1,2-h][1,7]naphthyridine 5 g of the title compound of melting point 130–131° C. are obtained by reaction of 20 g of (7R,8R,9R)-2,3-dimethyl-7,8-dihydroxy-9-phenyl-7,8,9,10-tetrahydroimidazo[1,2-h][1,7]-naphthyridine with 2-methoxyethanol according to example L, method a.

Q. (7S,8R,9R)-2,3-Dimethyl-8-hydroxy-7-(2-methoxyethoxy)-9-phenyl-7,8,9,10-tetrahydro-imidazo[1,2-h][1,7]naphthyridine 7.8 g of the title compound of melting point 131–132° C. are obtained as a solid from the mother liquor from example P after purification on silica gel (eluent: diethyl ether).

R. (7R,8R,9R)-2,3-Dimethyl-8-hydroxy-7-(2-methoxyethoxy)-9-phenyl-7H-8,9-dihydro-pyrano[2,3-h]imidazo[1,2-a]pyridine 0.51 ml (9.67 mmol) of sulfuric acid is added dropwise to a suspension of 1.50 g (4.83 mmol) of (7R,8R,9R)-2,3-dimethyl-7,8-dihydroxy-9-phenyl-7H-8,9-dihydropyrano[2,3-c]imidazo[1,2-a]-pyridine (WO 98/54188) in 2-methoxyethanol (7.0 ml). The mixture is subsequently stirred at 120° C. for 6 h. The mixture is then diluted with 100 ml of water, neutralized with saturated aqueous sodium hydrogencarbonate solution and extracted twice with dichloromethane. The combined organic phases are washed with salt water, dried over sodium sulfate and concentrated in vacuo. The crude product is purified by column chromatography (diethyl ether/triethylamine 1:1) and affords 0.40 g (1.08 mmol/22%) of the title compound as a colorless-solid of m.p. 155–157° C. (diethyl ether).

Commercial Applicability

The compounds of the formula 1 and their salts have valuable pharmacological properties which make them commercially utilizable. In particular, they exhibit pronounced inhibition of gastric acid secretion and an excellent gastric and intestinal protective action in warm-blooded animals, in particular humans. In this connection, the compounds according to the invention are distinguished by a high selectivity, an advantageous duration of action, a particularly good enteral activity, the absence of significant side effects and a large therapeutic breadth.

"Gastric and intestinal protection" in this connection is understood as meaning the prevention and treatment of gastrointestinal diseases, in particular of gastrointestinal inflammatory diseases and lesions, and of gastric acid-related diseases in mammals including man (such as, for example, gastric ulcers, duodenal ulcers, gastritis, hyperacidic or medicament-related functional gastropathy, reflux esophagitis, Zollinger-Ellison syndrome, heartburn), which can be caused, for example, by microorganisms (e.g. Helicobacter pylori), bacterial toxins, medicaments (e.g. certain antiinflammatories and antirheumatics), chemicals (e.g. ethanol), gastric acid or stress situations.

In their excellent properties, the compounds according to the invention surprisingly prove to be markedly superior to the compounds known from the prior art in various models in which the antiulcerogenic and the antisecretory properties are determined. On account of these properties, the compounds of the formula 1 and their pharmacologically tolerable salts are outstandingly suitable for use in human and veterinary medicine, where they are used, in particular, for the treatment and/or prophylaxis of disorders of the stomach and/or intestine.

The invention therefore further relates to the compounds according to the invention for use in the treatment and/or prophylaxis of the abovementioned diseases.

The invention likewise comprises the use of the compounds according to the invention for the production of medicaments which are employed for the treatment and/or prophylaxis of the abovementioned diseases.

The invention furthermore comprises the use of the compounds according to the invention for the treatment and/or prophylaxis of the abovementioned diseases.

The invention further relates to medicaments which contain one or more compounds of the formula 1 and/or their pharmacologically tolerable salts.

The medicaments are prepared by processes which are known per se and familiar to the person skilled in the art. As medicaments, the pharmacologically active compounds (=active compounds) according to the invention are either used as such, or preferably in combination with suitable pharmaceutical excipients or vehicles in the form of tablets, coated tablets, capsules, suppositories, patches (e.g. as TTS), emulsions, suspensions or solutions, the active compound content being advantageously between 0.1 and 95% and where a pharmaceutical administration form (e.g. a delayed-release form or an enteric form) exactly tailored to the active compound and/or to the desired onset of action and/or to the duration of action can be obtained by the appropriate choice of the excipients and vehicles.

The person skilled in the art knows, on the basis of his/her expert knowledge which excipients and vehicles are suitable for the desired pharmaceutical formulations. In addition to solvents, gel formers, suppository bases, tablet excipients and other active compound vehicles, it is possible to use, for example, antioxidants, dispersants, emulsifiers, antifoams, flavor corrigents, preservatives, solubilizers, colorants or in particular permeation promoters and complexing agents (e.g. cyclodextrins).

The active compounds can be administered orally, parenterally or percutaneously.

In general, it has proven advantageous in human medicine to administer the active compound(s) in the case of oral administration in a daily dose from approximately 0.01 to approximately 20, preferably 0.05 to 5, in particular 0.1 to 1.5, mg/kg of body weight, if appropriate in the form of a number of, preferably 1 to 4, individual administrations to obtain the desired result. In the case of parenteral treatment, similar or (in particular in the case of intravenous administration of the active compounds), as a rule, lower doses can be used. Any person skilled in the art can easily determine on the basis of his/her expert knowledge the optimal dose and manner of administration of the active compound necessary in each case.

If the compounds according to the invention and/or their salts are to be employed for the treatment of the abovementioned diseases, the pharmaceutical preparations can also contain one or more pharmacologically active constituents of other pharmaceutical groups. The following examples may be mentioned: tranquilizers (for example from the benzodiazepines group, e.g. diazepam), spasmolytics (e.g. bietamiverine or camylofine), anticholinergics (e.g. oxyphencyclimine or phencarbamide), local anesthetics (e.g. tetracaine or procaine), and, if appropriate, also enzymes, vitamins or amino acids.

To be emphasized in particular in this connection is the combination of the compounds according to the invention with pharmaceuticals which inhibit acid secretion, such as $H_2$ blockers (e.g. cimetidine, ranitidine), $H^+/K^+$ ATPase inhibitors (e.g. omeprazole, pantoprazole), or furthermore with so-called peripheral anticholinergics (e.g. pirenzepine, telenzepine) and with gastric antagonists with the aim of potentiating the main action in the additive orsuperadditive sense and/or of eliminating or lowering the side effects, or furthermore the combination with antibacterially active substances (such as cephalosporins, tetracyclines, penicillins, macrolides, nitroimidazoles or alternatively bismuth salts) for the control of Helicobacter pylori. Examples of antibacterially active combination components which may be mentioned are meziocillin, ampicillin, amoxicillin, cefalothin, cefoxitin, cefotaxime, imipenem, gentamycin, amikacin, erythromycin, ciprofloxacin, metronidazole, clarithromycin, azithromycin and combinations thereof (e.g. clarithromycin+metronidazole).

Pharmacology

The excellent gastric protective action and the gastric acid secretion-inhibiting action of the compounds according to the invention can be demonstrated in investigations in animal experimental models. The compounds according to the invention investigated in the model mentioned below have been provided with numbers which correspond to the numbers of these compounds in the examples.

Testing of the Secretion-inhibiting Action on Perfused Rat Stomach

In table A below, the influence of the compounds according to the invention after intravenous administration is shown on the acid secretion of the perfused rat stomach stimulated by pentagastrin.

TABLE A

| No. | Dose (µmol/kg) i.v. | Inhibition of acid secretion (%) |
|---|---|---|
| 1 | 3 | 100 |
| 2 | 3 | 100 |
| 3 | 3 | 100 |

Methodology

The abdomen of anesthetized rats (CD rats, female, 200–250 g; 1.5 g/kg of i.m. urethane) was opened after tracheotomy by a median upper abdominal incision and a PVC catheter was fixed transorally in the esophagus and a further one via the pylorus such that the ends of the tubing just still projected into the gastric lumen. The catheter leading from the pylorus led outwards via a side opening in the right abdominal wall.

After thorough rinsing (about 50–100 ml), a continuous flow of warm physiological NaCl solution (0.5 ml/min, pH 6.8–6.9; Braun-Unita I) was continuously passed through the stomach at 37° C. The pH in the effluent, in each case collected at an interval of 15 minutes, was determined (pH meter 632, glass electrode EA 147; φ 5 mm, Metrohm) and the secreted HCl was determined by titration with a freshly prepared 0.01N NaOH solution to pH 7 (Dosimat 665 Metrohm).

Gastric secretion was stimulated by continuous infusion of 1 µg/kg (=1.65 ml/h) of i.v. pentagastrin (left femoral vein) about 30 min after the end of the operation (i.e. after determination of 2 preliminary fractions). The substances to be tested were administered intravenously in 1 ml/kg of fluid volume 60 min after the start of the pentagastrin continuous infusion.

The body temperature of the animals was kept at a constant 37.8–38° C. by means of infrared irradiation and heating pads (automatic, step-free control via a rectal temperature sensor).

The invention claimed is:
1. A compound of the formula 1,

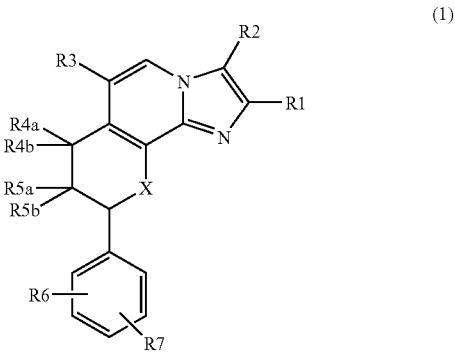

in which
R1 is methyl,
R2 is methyl,
R3 is hydrogen,
one of the substituents R4a and R4b is hydrogen and the other is 1–4C-alkoxy or 1–4C-alkoxy-1–4C-alkoxy,
R5a is the radical —OR',
R5b is hydrogen,
R6 is hydrogen,
R7 is hydrogen and
X is O (oxygen) or NH,
and where
R' is selected from the group consisting of
—C(O)—NR8R9,
—C(O)-alk-NR8R9,
—C(O)-alk-C(O)—NR8R9,
—P(O)(OH)2,
—S(O)2NR8R9,
—C(O)—R8,
—C(O)—C6H3R10R11,
—C(O)—OR8,
—C(O)-alk-C(O)—R8,
—C(O)-alk-C(O)—OR8,
—C(O)—C(O)—R8, and —C(O)—C(O)—OR8,
where
alk is 1–7C-alkylene,
R8 is hydrogen, 1–10C-alkyl or 1–4C-alkyl substituted by halogen, carboxyl, hydroxyl, sulfo (—SO3H), sulfamoyl (—SO2NH2), carbamoyl (—CONH2), 1–4C-alkoxy or 1–4C-alkoxycarbonyl,
R9 is hydrogen or 1–4C-alkyl,
R10 is hydrogen, halogen, nitro, 1–4C-alkyl, 1–4C-alkoxy, 1–4C-alkoxycarbonyl, 1–4C-alkoxycarbonylamino, 1–4C-alkoxy-1–4C-alkoxycarbonylamino or trifluoromethyl and
R11 is hydrogen, halogen, 1–4C-alkyl or 1–4C-alkoxy, with the proviso that when R5a is the radical —OR' and R' is COR8 then R8 is a member selected from the group consisting of hydrogen, a 1–4C-alkyl substituted by halogen, carboxyl, hydroxyl, sulfo (—SO3H), sulfamoyl (—SO2NH2), carbamoyl (—CONH2), 1–40-alkoxy, and a 1–4C-alkoxycarbonyl or a solvate, salt, or solvate of a salt thereof.

2. A compound as claimed in claim 1,
in which
R1 is methyl,
R2 is methyl,
R3 is hydrogen,
one of the substituents R4a and R4b is hydrogen and the other is 1–4C-alkoxy or 1–4C-alkoxy-1–4C-alkoxy,
R5a is the radical —OR',
R5b is hydrogen,
R6 is hydrogen,
R7 is hydrogen and
X is O (oxygen) or NH,
and where
R' is selected from the group consisting of
—C(O)—NR8R9,
—C(O)-alk-NR8R9,
—C(O)—R8,
—C(O)—C6H3R10R11,
—C(O)—OR8,
—C(O)-alk-C(O)—OR8, and
—C(O)—C(O)—OR8 where
alk is 1–4C-alkylene,
R8 is hydrogen, 1–4C-alkyl, 1–4C-alkyl substituted by 1–4C-alkoxy or menthyl,
R9 is hydrogen or 1–4C-alkyl,
R10 is hydrogen, halogen, nitro, 1–4C-alkyl, 1–4C-alkoxy, 1–4C-alkoxycarbonyl, or trifluoromethyl and
R11 is hydrogen or halogen,
or a solvate, salt, or solvate of a salt thereof.

3. A compound as claimed in claim 1,
in which
R1 is methyl,
R2 is methyl,
R3 is hydrogen,
one of the substituents R4a and R4b is hydrogen and the other is methoxyethoxy,
R5a is the radical —OR',
R5b is hydrogen,
R6 is hydrogen,
R7 is hydrogen and
X is NH,
and where
R' is selected from the group consisting of
—C(O)—NR8R9,
—C(O)-alk-NR8R9,
—C(O)—R8,
—C(O)C6H3R10R11,
—C(O)—OR8,
—C(O)-alk-C(O)—OR8, and
—C(O)—C(O)—OR8
where
alk is 1–4C-alkylene,
R8 is hydrogen, 1–4C-alkyl, 1–4C-alkyl substituted by 1–4C-alkoxy or menthyl,
R9 is hydrogen or 1–4C-alkyl,
R10 is hydrogen, halogen, nitro, 1–4C-alkyl, 1–4C-alkoxy, 1–4C-alkoxycarbonyl, or trifluoromethyl and
R11 is hydrogen or halogen,
or a solvate, salt, or solvate of a salt thereof.

4. A compound as claimed in claim 1,
in which
R1 is methyl,
R2 is methyl,
R3 is hydrogen,
one of the substituents R4a and R4b is hydrogen and the other is methoxyethoxy,
R5a is the radical—OR',
R5b is hydrogen,
R6 is hydrogen,
R7 is hydrogen and
X is NH,
and where
R' is selected from the group consisting of
—C(O)-alk-NR8R9,
—C(O)—R8,
—C(O)—OR8,
—C(O)-alk-C(O)—OR8, and
—C(O)—C(O)—OR8
where
alk is 1–4C-alkylene,
R8 is hydrogen, 1–4C-alkyl, 1–4C-alkyl substituted by 1–4C-alkoxy or menthyl,
R9 is hydrogen or 1–4C-alkyl,
or a solvate, salt, or solvate of a salt thereof.

5. A compound as claimed in claim 1,
in which
R1 is methyl,
R2 is methyl,
R3 is hydrogen,
one of the substituents R4a and R4b is hydrogen and the other is methoxyethoxy,
R5a is the radical —OR',
R5b is hydrogen,
R6 is hydrogen,
R7 is hydrogen and
X is NH,
and where
R' is selected from the group consisting of
—C(O)-alk-NR8R9,
—C(O)—R8,
where
alk is 1–4C-alkylene,
R8 is 1–4C-alkyl or 1–4C-alkyl substituted by 1–4C-alkoxy,
R9 is hydrogen or 1–4C-alkyl,
or a solvate, salt, or solvate of a salt thereof.

6. A compound as claimed in claim 1, having the formula 1*

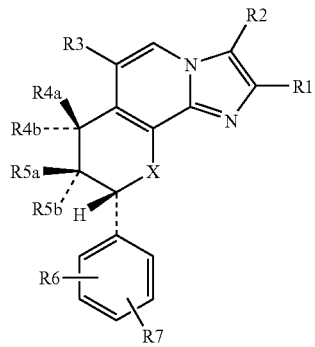

(1*)

in which
R1 is methyl,
R2 is methyl,
R3 is hydrogen,
one of the substituents R4a and R4b is hydrogen and the other is 1–4C-alkoxy or 1–4C-alkoxy-1–4C-alkoxy,
R5a is the radical —OR',
R5b is hydrogen,
R6 is hydrogen,
R7 is hydrogen and
X is O (oxygen) or NH,
and where
R' is selected from the group consisting of
—C(O)—NR8R9,
—C(O)-alk-NR8R9,
—C(O)—R8,
—C(O)—C$_6$H$_3$R10R11,
—C(O)—OR8,
—C(O)-alk-C(O)—OR8, and
—C(O)—C(O)—OR8 where
alk is 1–4C-alkylene,
R8 is hydrogen, 1–4C-alkyl, 1–4C-alkyl substituted by 1–4C-alkoxy or menthyl,
R9 is hydrogen or 1–4C-alkyl,
R10 is hydrogen, halogen, nitro, 1–4C-alkyl, 1–4C-alkoxy, 1–4C-alkoxycarbonyl, or trifluoromethyl and
R11 is hydrogen or halogen,
or a solvate, salt, or solvate of a salt thereof.

7. A compound as claimed in claim 1, which has the formula 1*

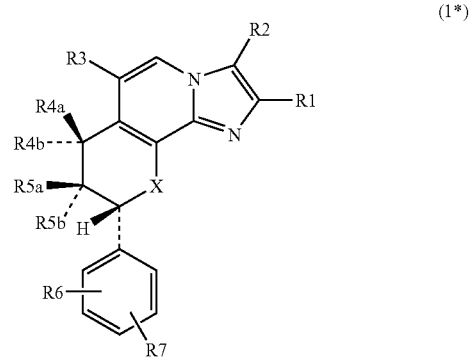

(1*)

in which
R1 is methyl,
R2 is methyl,
R3 is hydrogen,
one of the substituents R4a and R4b is hydrogen and the other is methoxyethoxy,
R5a is the radical —OR',
R5b is hydrogen,
R6 is hydrogen,
R7 is hydrogen and
X is NH,
and where
R' is selected from the group consisting of
—C(O)—NR8R9,
—C(O)-alk-NR8R9,
—C(O)—R8,
—C(O)—C$_6$H$_3$R10R11,
—C(O)—OR8,
—C(O)-alk-C(O)—OR8, and
—C(O)—C(O)—OR8
where
alk is 1–4C-alkylene,
R8 is hydrogen, 1–4C-alkyl, 1–4C-alkyl substituted by 1–4C-alkoxy or menthyl,
R9 is hydrogen or 1–4C-alkyl,
R10 is hydrogen, halogen, nitro, 1–4C-alkyl, 1–4C-alkoxy, 1–4C-alkoxycarbonyl, or trifluoromethyl and
R11 is hydrogen or halogen,
or a solvate, salt, or solvate of a salt thereof.

8. A compound as claimed in claim 1, which has the formula 1*

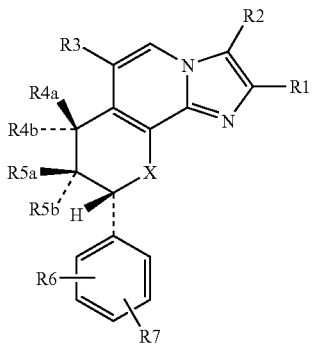

in which
R1 is methyl,
R2 is methyl,
R3 is hydrogen,
one of the substituents R4a and R4b is hydrogen and the other is methoxyethoxy,
R5a is the radical —OR',
R5b is hydrogen,
R6 is hydrogen,
R7 is hydrogen and
X is NH,
and where
R' is selected from the group consisting of
—C(O)-alk-NR8R9,
—C(O)—R8,
—C(O)—OR8,
—C(O)-alk-C(O)—OR8, and
—C(O)—C(O)—OR8
where
alk is 1–4C-alkylene,
R8 is hydrogen, 1–4C-alkyl, 1–4C-alkyl substituted by 1–4C-alkoxy or menthyl,
R9 is hydrogen or 1–4C-alkyl,
or a solvate, salt, or solvate of a salt thereof.

9. A compound as claimed in claim 1, which has the formula 1*

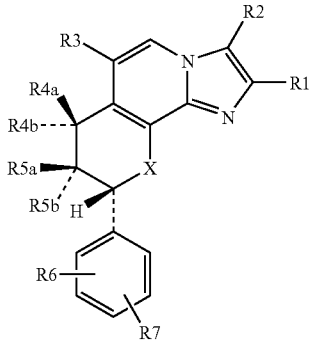

in which
R1 is methyl,
R2 is methyl,
R3 is hydrogen,
one of the substituents R4a and R4b is hydrogen and the other is methoxyethoxy,
R5a is the radical —OR',
R5b is hydrogen,
R6 is hydrogen,
R7 is hydrogen and
X is NH,
and where
R' is selected from the group consisting of
—C(O)-alk-NR8R9,
—C(O)—R8,
where
alk is 1–4C-alkylene,
R8 is 1–4C-alkyl or 1–4C-alkyl substituted by 1–4C-alkoxy,
R9 is hydrogen or 1–4C-alkyl,
or a solvate, salt, or solvate of a salt thereof.

10. A compound which is (7R,8R,9R)-7-(2-Methoxyethoxy)-2,3-dimethyl-8-(N,N-dimethylaminomethyl-carbonyloxy)-9-phenyl-7,8,9,10-tetrahydroimidazo[1,2-h][1,7]naphthyridine, or a solvate, salt, or solvate of a salt thereof.

11. A pharmaceutical composition comprising a therapeutically effective amount of a compound of claim 1 and/or a pharmacologically tolerable solvate, salt, or solvate of a salt thereof together with customary pharmaceutical excipients and/or vehicles.

12. A pharmaceutical composition comprising a therapeutically effective amount of (7R,8R,9R)-7-(2-Methoxyethoxy)-2,3-dimethyl-8-(N,N-dimethyl-aminomethyl-carbonyloxy)-9-phenyl-7,8,9,10-tetrahydroimidazo-[1,2-h][1,7]naphthyridine, and/or a pharmacologically tolerable solvate, salt, or solvate of a salt thereof together with customary pharmaceutical excipients and/or vehicles.

13. A method of treating a gastrointestinal disorder caused by gastric acid in a patient comprising administering to a patient in need thereof a therapeutically effective amount of the compound as claimed in claim 1 and/or a pharmacologically tolerable solvate, salt, or solvate of a salt thereof.

14. A method of treating a gastrointestinal disorder caused by gastric acid in a patient comprising administering to a patient in need thereof a therapeutically effective amount of (7R,8R,9R)-7-(2-Methoxyethoxy)-2,3-dimethyl-8-(N,N-dimethyl-aminomethyl-carbonyloxy)-9-phenyl-7,8,9,10-tetrahydroimidazo-[1,2-h][1,7]naphthyridine and/or a pharmacologically tolerable, solvate, salt, or solvate of a salt thereof.

15. The method according to claim 13, wherein the gastrointestinal disorder caused by gastric acid is selected from the group consisting of gastric ulcer, duodenal ulcer, gastritis, hyperacidic functional gastropathy, medicament-related functional gastropathy, reflux esophagitis, Zollinger-Ellison syndrome, heartburn and peptic ulcer bleeding.

16. The method according to claim 14, wherein the gastrointestinal disorder caused by gastric acid is selected from the group consisting of gastric ulcer, duodenal ulcer, gastritis, hyperacidic functional gastropathy, medicament-related functional gastropathy, reflux esophagitis, Zollinger-Ellison syndrome, heartburn and peptic ulcer bleeding.

* * * * *

UNITED STATES PATENT AND TRADEMARK OFFICE
CERTIFICATE OF CORRECTION

PATENT NO. : 7,189,736 B2
APPLICATION NO. : 10/826337
DATED : March 13, 2007
INVENTOR(S) : Senn-Bilfinger et al.

It is certified that error appears in the above-identified patent and that said Letters Patent is hereby corrected as shown below:

Claim 1, Column 35, Lines 43-44,
Please delete

" 1-40-alkoxy " and replace with

-- 1-4C-alkoxy --

Signed and Sealed this

First Day of May, 2007

JON W. DUDAS
*Director of the United States Patent and Trademark Office*